US008044032B2

(12) United States Patent
Shir et al.

(10) Patent No.: US 8,044,032 B2
(45) Date of Patent: Oct. 25, 2011

(54) SELECTIVE KILLING OF CELLS BY ACTIVATION OF DOUBLE-STRANDED RNA DEPENDENT PROTEIN KINASE-PKR

(75) Inventors: Alexei Shir, Jerusalem (IL); Alexander Levitzki, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 935 days.

(21) Appl. No.: 11/540,505

(22) Filed: Oct. 2, 2006

(65) Prior Publication Data

US 2007/0036764 A1 Feb. 15, 2007

Related U.S. Application Data

(62) Division of application No. 10/182,269, filed as application No. PCT/IL01/00094 on Jan. 31, 2001, now abandoned.

(60) Provisional application No. 60/258,010, filed on Dec. 22, 2000, provisional application No. 60/179,361, filed on Jan. 31, 2000.

(51) Int. Cl.
*C12N 15/11* (2006.01)
(52) U.S. Cl. .................................. 514/44 A
(58) Field of Classification Search .................. 514/44 A
See application file for complete search history.

(56) References Cited

U.S. PATENT DOCUMENTS

| 5,624,803 | A | 4/1997 | Noonberg et al. |
| 5,734,039 | A | 3/1998 | Calabretta et al. |
| 5,955,306 | A | 9/1999 | Gimeno et al. |
| 5,994,314 | A | 11/1999 | Eljamal et al. |
| 5,997,858 | A | 12/1999 | Tovey et al. |
| 6,150,110 | A | 11/2000 | Fletcher et al. |
| 2003/0153083 | A1 | 8/2003 | Shir et al. |

FOREIGN PATENT DOCUMENTS

| WO | WO 92/22303 | 12/1992 |
| WO | WO 96/18733 | 6/1996 |
| WO | WO 97/17456 | 5/1997 |
| WO | WO 98/54315 | 12/1998 |
| WO | WO 01/57205 | 9/2001 |

OTHER PUBLICATIONS

Agrawal et al. "Antisense Therapeutics: Is It as Simple as Complementary Base Recognition?", Molecular Medicine Today: Reviews, 61: 72-81, 2000.
Opalinska et al. "Nucleic-Acid Therapeutics: Basic Principles and Recent Applications", Nature Reviews: Drug Discovery, 1: 503-514, 2002.
Jen et al. "Suppression of Gene Expression by Targeted Disruption of Messenger RNA: Available Options and Current Strategies", Stem Cells, 18: 307-319, 2000.
Crooke "Progress in Antisense Technology", Annual Reviews in Medicine, 55: 61-95, 2004.
Deglon et al, "Self-Inactivating Lentiviral Vectors with Enhanced Transgene Expression as Potential Gene Transfer System in Parkinson's Disease", *Human Gene Therapy*, 11:179-190, 2000.
Manche et al, "Interactions Between Double-Stranded RNA Regulators and the Protein Kinase DAI", *Molecular and Cellular Biology*, 12(11):5238-5248, 1992.
Jagus et al, "PKR, Apoptosis and Cancer", *Int'l J. of Biochem and Cell Biol.*, 31:123-138, 1999.
Yukai et al, "Inhibition of Human Squamous Cell Carcinoma Growth In Vivi by Epidermal Growth factor Receptor Antisense RNA Transcribed From the bU6 Promoter", *J. Nat'l Cancer Inst.*, 90(14):1080-1087, 1998.
Ben-Asouli et al, "Human Interferon-Gamma mRNA Regulates its own Translation Through local Activation of the Protein Kinase PKR", *J. Interferon and Cytokine Research*, 19(Supp 1):S101, 1999.
Asubel et al,Eds., A Compendium of Methods from Current Protocols in Molecular Biology, John Wiley & Sons, Inc., Chap. 6, 1992.
Balachandran et al, "Activation of the dsRNA-dependent protein kinase, PKR, induces apoptosis through FADD-mediated death signaling", *EMBO J.* Dec. 1, 1998;17(23):6888-902.
Davies et al, "The vaccinia virus K3L gene product potentiates translation by inhibiting double-stranded-RNA-activated protein kinase and phosphorylation of the alpha subunit of eukaryotic initiation factor 2", *J Virol.* Apr. 1992;66(4):1943-50.
Cleary et al, "Cloning and structural analysis of cDNAs for bc1-2 and a hybrid bcl-2/immunoglobulin transcript resulting from the t(14;18) translocation", *Cell.* Oct. 10, 1986;47(1):19-28.
Clemens, MJ, "Regulation of eukaryotic protein synthesis by protein kinases that phosphorylate initiation factor eIF-2", *Mol Biol Rep.* May 1994;19(3):201-10.
Clemens et al, "Inhibition of protein synthesis in rabbit reticulocyte lysates by double-stranded RNA and oxidized glutathione: indirect mode of action on polypeptide chain initiation", *Proc Natl Acad Sci U S A.* Apr. 1975;72(4):1286-90.
Corry, S., "Activation of cellular oncogenes in hemopoietic cells by chromosome translocation", *Adv Cancer Res.* 1986;47:189-234.
Davies et al, "The E3L and K3L vaccinia virus gene products stimulate translation through inhibition of the double-stranded RNA-dependent protein kinase by different mechanisms", *J Virol.* Mar. 1993;67(3):1688-92.
Zufferey et al, "Multiply attenuated lentiviral vector achieves efficient gene delivery in vivo", *Nat Biotechnol.* Sep. 1997;15(9):871-5.

(Continued)

*Primary Examiner* — J. E. Angell

(57) ABSTRACT

Novel methods and compositions for selective killing of cells by activation of PKR are disclosed. In a preferred embodiment, a method is provided for causing cell death in a targeted population of cells that includes the steps of: selecting a nucleotide sequence at a single genetic locus in the targeted population that is absent from the equivalent locus in a population of non-targeted cells; obtaining one or more anti-sense RNA having sequence homology with the locus in the targeted population; permitting the anti-sense RNA to hybridize with an RNA transcribed from the locus in the targeted population so as to form a contiguous double stranded RNA for interacting with PKR. The activation of PKR gives rise to selective cell death in the targeted population.

13 Claims, 12 Drawing Sheets

OTHER PUBLICATIONS

Donze et al, "Abrogation of translation initiation factor eIF-2 phosphorylation causes malignant transformation of NIH 3T3 cells", *EMBO J.* Aug. 1, 1995;14(15):3828-34.

Edwards et al, "A simple and rapid method for the preparation of plant genomic DNA for PCR analysis", *Nucleic Acids Res.* Mar. 25, 1991;19(6):1349.

Farrell et al, "Phosphorylation of initiation factor eIF-2 and the control of reticulocyte protein synthesis", *Cell.* May 1977;11(1):187-200.

Fischer et al, "A Ki-1 (CD30)-positive human cell line (Karpas 299) established from a high-grade non-Hodgkin's lymphoma, showing a 2;5 translocation and rearrangement of the T-cell receptor beta-chain gene", *Blood.* Jul. 1988;72(1):234-40.

He et al, "Growth Inhibition of Human Papillomavirus 16 DNA-Positive Mouse Tumor by Antisense RNA Transcribed form U6 Promoter", *Cancer Research*, 57:3993-9, 1997.

He et al, "Inhibition of human squamous cell carcinoma growth in vivo by epidermal growth factor receptor antisense RNA transcribed from the U6 promoter", *J Natl Cancer Inst.* Jul. 15, 1998;90(14):1080-7. Erratum in: *J Natl Cancer Inst* Apr. 17, 2002;94(8):633.

Hunter et al, "The characteristics of inhibition of protein synthesis by double-stranded ribonucleic acid in reticulocyte lysates", *J Biol Chem.* Jan. 25, 1975;250(2):409-17.

Hurwitz et al, "Characterization of a leukemic cell line of the pre-B phenotype", *Int J Cancer.* Feb. 1979;23(2):174-80.

Jagus et al, "PKR, Apopstosis and Cancer", *Int. J. Biochem. & Cell Biol.*, 31:123-138, 1999.

Jereb et al, "Addition of IFN-alpha to treatment of malignant brain tumors", *Acta Oncol.* 1994;33(6):651-4.

Koromilas et al, "Malignant transformation by a mutant of the IFN-inducible dsRNA-dependent protein kinase", *Science.* Sep. 18, 1992;257(5077):1685-9.

Kunkel et al, "Transcription of a human U6 small nuclear RNA gene in vivo withstands deletion of intragenic sequences but not of an upstream TATATA box.", *Nucleic Acids. Res.* Sep. 25, 1989;17(18):7371-9.

Lee et al, "The interferon-induced double-stranded RNA-activated protein kinase induces apoptosis", *Virology.* Mar. 1994;199(2):491-6.

Levin et al, "Characterization of double-stranded-RNA-activated kinase that phosphorylates alpha subunit of eukaryotic initiation factor 2 (eIF-2 alpha) in reticulocyte lysates", *Proc Natl Acad Sci U S A.* Feb. 1980;77(2):832-6.

Levin et al, "Regulation of Protein Synthesis: Activation by double-stranded RNA of a Protein Kinase that Phosphorylates initiation factor 2", *Proc Natl Acad Sci U S A.*, 75(3):1121-1125, 1978.

Morris et al, "Fusion of a kinase gene, ALK, to a nucleolar protein gene, NPM, in non-Hodgkin's lymphoma", *Science.* Jan. 20, 1995;267(5196):316-7.

Naldini et al, "In vivo gene delivery and stable transduction of nondividing cells by a lentiviral vector", *Science.* Apr. 12, 1996;272(5259):263-7.

Nishikawa et al, "A mutant epidermal growth factor receptor common in human glioma confers enhanced tumorigenicity", *Proc Natl Acad Sci U S A.* Aug. 2, 1994;91(16):7727-31.

Ong et al, "Chromosomal Abnormalities and Molecular Genetics of Non-Hidgkins Lymphoma", *Seminars in Oncology*, 25(4) 447-460, 1998.

Pain, VM, "Initiation of protein synthesis in eukaryotic cells", *Eur J Biochem.* Mar. 15, 1996;236(3):747-71.

Patel et al, "PACT, a protein activator of the interferon-induced protein kinase, PKR", *EMBO J.* Aug. 3, 1998;17(15):4379-90.

Sood et al, "A mammalian homologue of GCN2 protein kinase important for translational control by phosphorylation of eukaryotic initiation factor-2alpha", *Genetics.* Feb. 2000;154(2):787-801.

Tsujumoto et al, "Cloning of the chromosome breakpoint of neoplastic B cells with the t(14;18) chromosome translocation", *Science.* Nov. 30, 1984;226(4678):1097-9.

Bakhshi et al, "Cloning the chromosomal breakpoint of t(14;18) human lymphomas: clustering around JH on chromosome 14 and near a transcriptional unit on 18", *Cell.* Jul. 1985;41(3):899-906.

Wu et al, "A model for the double-stranded RNA (dsRNA)-dependent dimerization and activation of the dsRNA-activated protein kinase PKR", *J Biol Chem.* Jan. 10, 1997;272(2):1291-6.

Ekstrand et al. "Amplified and Rearranged Epidermal Growth Factor Receptor Genes in Human Glioblastomas Reveal Deletions of Sequences Encoding Portions of the N- and/or C-Terminal Tails", Proc. Natl. Acad. Sci., 89: 4309-4313, 1992. vol. 1.

Ponten et al. "Long Term Culture of Normal and Neoplastic Human Glia", Acta Path. Microbiol. 74: 465-486, 1968. vol. 1.

Requisition by the Examiner Dated Mar. 9, 2010 From the Canadian Intellectual Property Office Re.: Application No. 2,398,678.

Ausubel et al. "A Compendium of Methods From Current Protocols in Molecular Biology", John Wiley & Sons, Inc., Chap.6, 1992.

Balachandran et al. "Activation of the DsRNA-Dependent Protein Kinase, PKR, Induces Apoptosis Through FADD-Mediated Death Signaling", EMBO Journal, 17(23): 6888-6902, 1998.

Ben-Asouli et al. "Human Interferon-Gamma mRNA Regulates Its Own Translation Through Local Activation of the Protein Kinase PKR", Journal of Interferon and Cytokine Research, 19(Suppl.1): S101, 1999.

Cleary et al. "Cloning and Structural Analysis of cDNAs for Bcl-2 and A Hybrid Bcl-2/Immunoglobulin Transcript Resulting From the T(14;18) Translocation", Cell, 47(1): 19-28, 1986.

Clemens "Regulation of Eukaryotic Protein Synthesis by Protein Kinases That Phosphorylate Initiation Factor EIF-2", Molecular Biology Reports, 19(3): 201-210, 1994.

Clemens et al. "Inhibition of Protein Synthesis in Rabbit Reticulocyte Lysates by Double-Stranded RNA and Oxidized Glutathione: Indirect Mode of Action on Polypeptide Chain Initiation", Proc. Natl. Acad. Sci. USA, 72(4): 1286-1290, 1975.

Corry "Activation of Cellular Oncogenes in Hemopoietic Cells by Chromosome Translocation", Advanced Cancer Research, 47: 189-234, 1986.

Davies et al. "The E3L and K3L Vaccinia Virus Gene Products Stimulate Translation Through Inhibition of the Double-Stranded RNA-Dependent Protein Kinase by Different Mechanism", Journal of Virology, 67(3): 1688-1692, 1993.

Davies et al. "The Vaccinia Virus K3L Gene Product Potentiates Translation by Inhibiting Double-Stranded-RNA-Activated Protein Kinase and Phosphorylation of the Alpha Subunit of Eukaryotic Initiation Factor 2", Journal of Virology, 66(4): 1943-1950, 1992.

Deglon et al. "Self-Inactivating Lentiviral Vectors With Enhanced Transgene Expression as Potential Gene Transfer System in Parkinson's Disease", Human Gene Therapy, 11(1): 179-190, 2000.

Donze et al. "Abrogation of Translation Initiation Factor EIF-2 Phosphorylation Causes Malignant Transformation of NIH 3T3 Cells", EMBO Journal, 14(15): 3828-3834, 1995.

Edwards et al. "A Simple and Rapid Method for the Preparation of Plant Genomic DNA for PCR Analysis", Nucleic Acids Research, 19(6): 1349, 1991.

Ekstrand et al. "Amplified and Rearranged Epidermal Growth Factor Receptor Genes in Human Glioblastomas Reveal Deletions of Sequences Encoding Portions of the N- and/or C-Terminal Tails", Proc. Natl. Acad. Sci. USA, 89: 4309-4313, 1992.

Farrell et al. "Phosphorylation of Initiation Factor EIF-2 and the Control of Reticulocyte Protein Synthesis", Cell, 11(1): 187-200, 1977.

Fischer et al. "A Ki-1 (CD30)-Positive Human Cell Line (Karpas 299) Established From A High-Grade Non-Hodgkin's Lymphoma, Showing A 2;5 Tanslocation and Rearrangement of the T-Cell Receptor Beta-Chain Gene", Blood, 71(1): 234-240, 1988.

He et al. "Growth Inhibition of Human Papillomavirus 16 DNA-Positive Mouse Tumor by Antisense RNA Transcribed Form U6 Promoter", Cancer Research, 57: 3993-3999, 1997.

He et al. "Inhibition of Human Squamous Cell Carcinoma Growth In Vivo by Epidermal Growth Factor Receptor Antisense RNA Transcribed From the U6 Promoter", Journal of the National Cancer Institute, 90(14): 1080-1087, 1998.

Hunter et al. "The Characteristics od Inhibition of Protein Synthesis by Double-Stranded Ribonucleic Acid in Reticulocyte Lysates", The Journal of Biological Chemistry, 250(2): 409-417, 1975.

Hurwitz et al. "Characterization of A Leukemic Cell Line of the Pre-B Phenotype", Inernational Journal of Cancer, 23(2): 174-180, 1979.

Jagus et al. "PKR, Apoptosis and Cancer", International Journal of Biochemistry and Cell Biology, 31: 123-138, 1999.

Jereb et al. "Addition of IFN-Alpha to Treatment of Malignant Brain Tumors", Acta Oncologica, 33(6): 651-654, 1994.

Koromilas et al. "Malignat Transformation by A Mutant of the IFN-Inducible DsRNA-Dependent Protein Kinase", Science, 257(5077): 1685-1689, 1992.

Kunkel et al. "Transcription of A Human U6 Small Nuclear RNA Gene In Vivo Withstands Deletion of Intragenic Sequences But Not of an Upstream TATATA Box", Nucleic Acids Research, 17(18): 7371-7379, 1989.

Lee et al. "The Interferon-Induced Double-Stranded RNA-Activated Protein Kinase Induces Apoptosis", Virology, 199(2): 491-496, 1994.

Levin et al. "Characterization of Double-Stranded-RNA-Activated Kinase That Phosphorylates Alpha Subunit of Eukaryotic Initiation Factor 2 (EIF-2 Alpha) in Reticulocyte Lysates", Proc. Natl. Acad. Sci. USA, 77(2): 832-836, 1980.

Manche et al. "Interactions Between Double-Stranded RNA Regulators and the Protein Kinase DAI", Molecular and Cellular Biology, 12(11): 5238-5248, 1992.

Morris et al. "Fusion of A Kinase Gene, ALK, to A Nucleolar Protein Gene, NPM, in Non-Hodgkin's Lymphoma", Science, 267(5196): 316-317, 1995.

Naldini et al. "In Vivo Gene Delivery and Stable Transduction of Nondividing Cells by A Lentiviral Vector", Science, 272(5259): 263-267, 1996.

Nishikawa et al. "A Mutant Epidermal Growth Factor Receptor Common in Human Glioma Confers Enhanced Tumorigenicity", Proc. Natl. Acad. Sci. USA, 91(16): 7727-7731, 1994.

Ong et al. "Chromosomal Abnormalities and Molecular Genetics of Non-Hodgkin's Lymphoma", Seminars in Oncology, 25(4): 447-460, 1998.

Pain "Initiation of Protein Synthesis in Eukaryotic Cells", European Journal of Biochemistry, 236(3): 747-771, 1996.

Patel et al. "PACT, A Protein Activator of the Interferon-Induced Protein Kinase, PKR", EMBO Journal, 17(15): 4379-4390, 1998.

Ponten et al. "Long Term Culture of Normal and Neoplastic Human Glia", Acta Pathologia Microbiologia Scandinavia, 74: 465-486, 1968. Abstract.

Sood et al. "A Mammalian Homologue of GCN2 Protein Kinase Important for Translational Control by Phosphorylation of Eukaryotic Initiation Factor-2Alpha", Genetics, 154(2): 787-801, 2000.

Tsujiomoto et al. "Cloning of the Chromosome Breakpoint of Neoplastic B Cells With the T(14;18) Chromosome Translocation", Science, 226(4678): 1097-1099, 1984.

Wu et al. "A Model for the Double-Stranded RNA (DsRNA)-Dependent Dimerization and Activation of the DsRNA-Activated Protein Kinase PKR", Journal of Biological Chemistry, 272(2): 1291-1296, 1997.

Zufferey et al. "Multiply Attenuated Lentiviral Vector Achieves Efficient Gene Delivery In Vivo", Nature Biotechnology, 15(9): 871-875, 1997.

Official Action Dated May 1, 2006 From the US Patent and Trademark Office Re.: U.S. Appl. No. 10/182,269.

Office Action Dated May 17, 2009 From the Israeli Patent Office Re.: Application No. 150935 and Its Translation Into English.

Office Action Dated Nov. 20, 2008 From the Israeli Patent Office Re.: Application No. 150935 and Its Translation Into English.

Official Action Dated Jan. 14, 2010 From the US Patent and Trademark Office Re.: U.S. Appl. No. 11/540,505.

Office Action Dated Sep. 7, 2010 From the Israel Patent Office Re. Application No. 204416 and Its Translation Into English.

Levin et al. "Regulation of Protein Synthesis: Activation by Double-Stranded RNA of A Protein Kinase That Phosphorylates Initiation Factor 2", Proc. Natl. Acad. Sci. USA, 75(3): 1121-1125, 1978.

Nishikawa et al. "A Mutant Epidermal Growth Factor Receptor Common in IIuman Glioma Confers Enhanced Tumorigenicity", Proc. Natl. Acad. Sci. USA, 91(16): 7727-7731, 1994.

| U87MGdEGFR | | U87MG |
|---|---|---|
|  | Untreated |  |
|  | Sense |  |
|  | Antisense |  |
|  | IFN |  |
|  | Sense+IFN |  |
|  | Antisense+IFN |  |

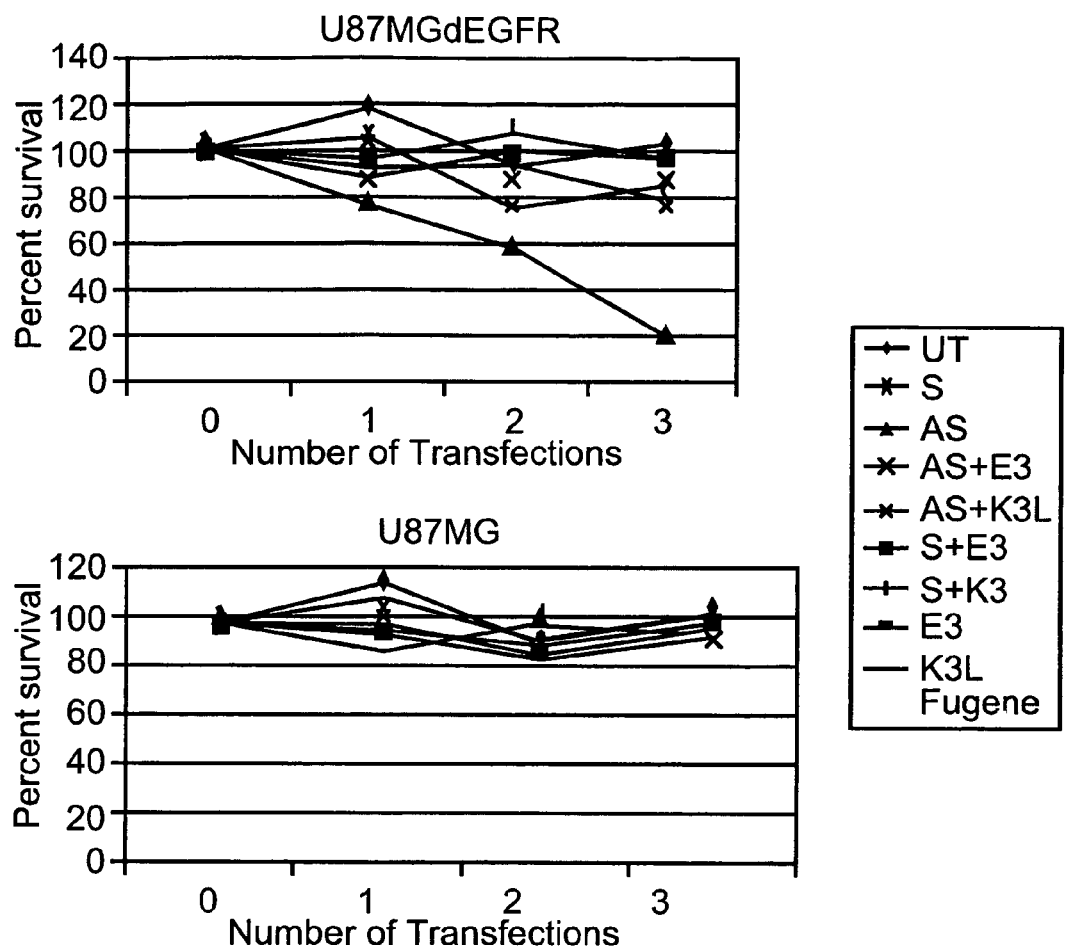
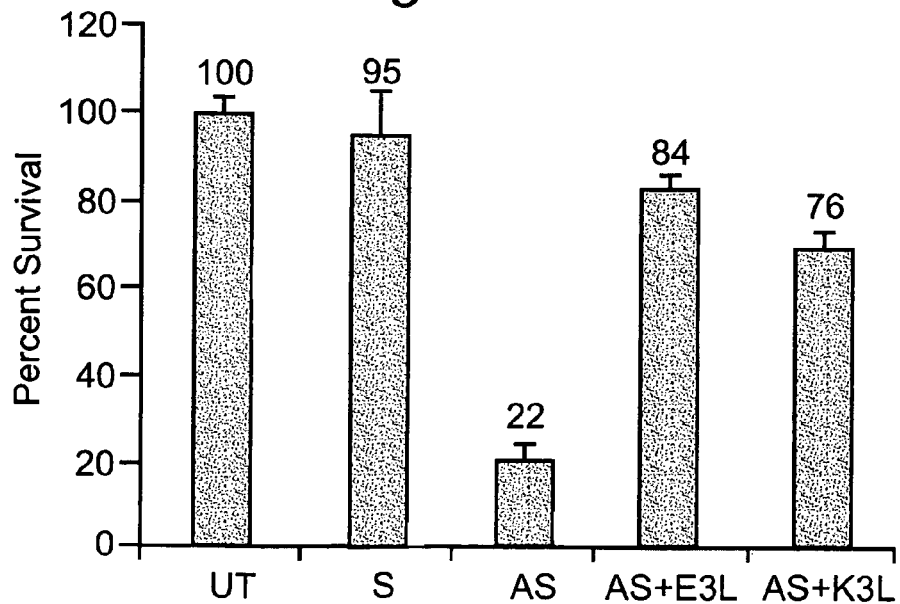
Fig. 8a
Fig. 8b

The effect of IFN-α on PKR expression

US 8,044,032 B2

SELECTIVE KILLING OF CELLS BY ACTIVATION OF DOUBLE-STRANDED RNA DEPENDENT PROTEIN KINASE-PKR

RELATED APPLICATIONS

This application is a divisional of U.S. patent application Ser. No. 10/182,269 filed on Nov. 15, 2002, which is a National Phase of PCT Patent Application No. PCT/IL01/00094 having International Filing Date of Jan. 31, 2001, which claims the benefit of U.S. Provisional Patent Application No. 60/258,010 filed on Dec. 22, 2000 and U.S. Provisional Patent Application No. 60/179,361 filed on Jan. 31, 2000. The contents of the above Applications are all incorporated herein by reference.

TECHNICAL FIELD

Compositions and methods are provided for activating double stranded RNA dependent protein kinase that includes an anti-sense RNA with sequence homology with a locus in a target cell characterized by a mutation, that is absent in non-target cells.

BACKGROUND OF THE INVENTION

Double stranded RNA dependent protein kinase (PKR) is a member of a family of kinases that phosphorylates the alpha subunit of protein synthesis initiation factor, eIF-2 (eIF-2α) and plays a role in the translational down regulation of gene expression (Clemens et al. Mol. Biol. Rep. 1994; vol. 19: 210-10). Activation of PKR involves two molecules binding in tandem to double stranded RNA and then phosphorylating each other in an intramolecular event. (Wu et al. 1997, J. Biol. Chem 272:1291-1296). PKR has been implicated in processes that rely on apoptosis as control mechanisms in vivo including antiviral activities, cell growth regulation and tumorigenesis (Donze et al. EMBO J. 1995, vol. 14: 3828-34; Lee et al. Virology 1994, vol. 199: 491-6; Jagus et al. Int. J. Biochem. Cell. Biol. 1989, vol. 9: 1576-86).

The alpha subunit of protein synthesis initiation factor is responsible for binding the initiating methionyl-tRNA (Met-tRNA$_f$), together with a molecule of GTP, and placing Met-tRNA$_f$ on native 40S ribosomal subunits (Pain, Eur. J. Biochem 1996, vol. 236; 747-771). During the course of this process GTP is hydrolyzed to GDP and inorganic phosphate, and when eIF-2 leaves the ribosome later in initiation (at the 60S subunit joining stage), it does so as an inactive eIF-2.GDP complex. Regeneration of active eIF-2 requires the exchange the GDP for a new molecule of GTP, catalyzed by the guanine nucleotide exchange factor eIF-2α (Pain, 1996). When eIF-2 becomes phosphorylated by PKR the initiation factor acquires an increased affinity for eIF-2α resulting in sequestration of the latter in an inactive complex. Consequently, the rate of guanine nucleotide exchange on both phosphorylated and unphosphorylated eIF-2 is decreased, as the concentration of available eIF-2α present in cell is reduced with respect to eIF-2, resulting in inhibition of polypeptide chain initiation. Not only does PKR activity have an effect on global rate of protein synthesis, but it may also selectively inhibit the translation of specific mRNAs that for various reasons have a greater than average requirement for active eIF-2 in the cell.

Regulation of protein synthesis through activated PKR arises from the interaction of PKR with double stranded RNA (dsRNA). The activation of PKR by dsRNA depends on the concentration and size of the dsRNA. In particular, PKR is activated by low levels of dsRNA and inhibited by higher levels of dsRNA. This gives rise to a characteristic bell-shaped curve for activation of the enzyme as a function of dsRNA concentration (Clemens et al., Proc. Natl. Acad. Sci. USA 1975; 72(4):1286-90; Levin D H. et al., Proc. Natl. Acad. Sci. USA 1980; 77(2):832-6 5). With respect to size of dsRNA, it has been found that molecules shorter than 30 base pairs (bp) in size fail to form a stable complex with PKR and do not activate the enzyme. Molecules longer than 30 bp bind and activate the enzyme, with an efficiency that increases with increasing chain length, reaching a maximum at about 85 bp. Analysis of complexes between dsRNA and PKR suggests that at maximal packing, the enzyme interacts with as little as a single helical turn of dsRNA (11 bp) but under conditions that allow activation, the binding site protects about 80 bp of duplex (Manche et al. Mol. Cell. Biol. 1992, vol. 12:5238-48).

SUMMARY

Novel methods and compositions for selective killing of cells by activation of PKR are provided. In a preferred embodiment of the invention, a method is provided for causing cell death in a targeted population of cells that includes the steps of: selecting a nucleotide sequence at a single genetic locus in the targeted population that is absent from the equivalent locus in a population of non-targeted cells; obtaining one or more anti-sense RNA having sequence homology with the locus in the targeted population; permitting the anti-sense RNA to hybridize with an RNA transcribed from the locus in the targeted population so as to form a contiguous double stranded RNA for interacting with PKR. The activation of PKR gives rise to selective cell death in the targeted population.

In a further embodiment of the invention, a method is provided for treating a subject having a disorder characterized by proliferating cells, that includes selecting a nucleotide sequence at a single genetic locus in the proliferating cells that differs from the equivalent locus in a population of non-proliferating cells: administering an effective amount of a nucleic acid so as to provide anti-sense RNA having sequence homology with the locus in the proliferating cells, such that the resultant double stranded RNA has a length suited for activating PKR; and treating the disorder in the subject by selectively killing the proliferating cells.

In a further embodiment of the invention, a pharmaceutical composition is provided for treating proliferative disorders, comprising: an effective tumor cell growth inhibiting amount of anti-sense RNA having a nucleotide sequence with a length of at least 30 nucleotides that is complementary to contiguous mRNA sequence in a neoplastic cell, the mRNA being absent in a non-neoplastic cell, the resulting double stranded RNA in the neoplastic cell activating a double stranded RNA dependent protein kinase.

In a further embodiment of the invention, an anti-sense RNA is provided that includes a natural or synthetic molecule having a length of at least 35 nucleotides, and having a sequence that is capable of hybridizing in situ to a contiguous nucleotide sequence that spans a site specific mutation on a mammalian chromosome.

In a further embodiment of the invention, a nucleic acid is provided that includes a sequence that is a template for an anti-sense RNA, wherein the anti-sense RNA hybridizing to a messenger RNA, the messenger RNA being transcribed from a contiguous nucleotide sequence that spans a site specific mutation on a mammalian chromosome, the mutation occurring in a neoplastic cell and absent in a non-neoplastic cell, the nucleic acid having a length of at least 30 nucleotides, and more particularly 85 nucleotides, and no greater than 100 nucleotides.

In a further embodiment of the invention, a vector is provided more particular a retroviral vector, more particularly a lentiviral vector that includes a sequence of nucleotides that is a template for an anti-sense RNA of a length greater than about 30 nucleotides and less than 100 nucleotides, more particularly in the range of 35 through 85 nucleotides, wherein the anti-sense RNA hybridizes under stringent conditions to a messenger RNA, the messenger RNA being transcribed from a contiguous nucleotide sequence that spans a site specific mutation on a mammalian chromosome, the mutation being a distinguishing characteristic of a neoplastic cell, the mutation being absent on non-neoplastic cells.

In a further embodiment of the invention, a cell population is provided which is transfected with a vector according to the above description. More particularly, the transfection is a stable transfection and the cell population is maintained in cell culture medium.

BRIEF DESCRIPTION OF THE FIGURES

FIG. 8 shows the effect of triple transfection with one or a combination of plasmids as indicated on survival of glioblastoma cells. (A)(i) U87MGΔEGFR and (A)(ii) U87MG. (B) U87MGΔEGFR cells after the third transfection.

FIGS. 12a-b shows the rescue of the U87MGΔEGFR cells by NCR inhibitors. (a) Effect of 2-Aminopurine on survival of cells in percentages. (b) The raw OD data of FIG. 12a.

DETAILED DESCRIPTION OF SPECIFIC EMBODIMENTS

Figure 1:
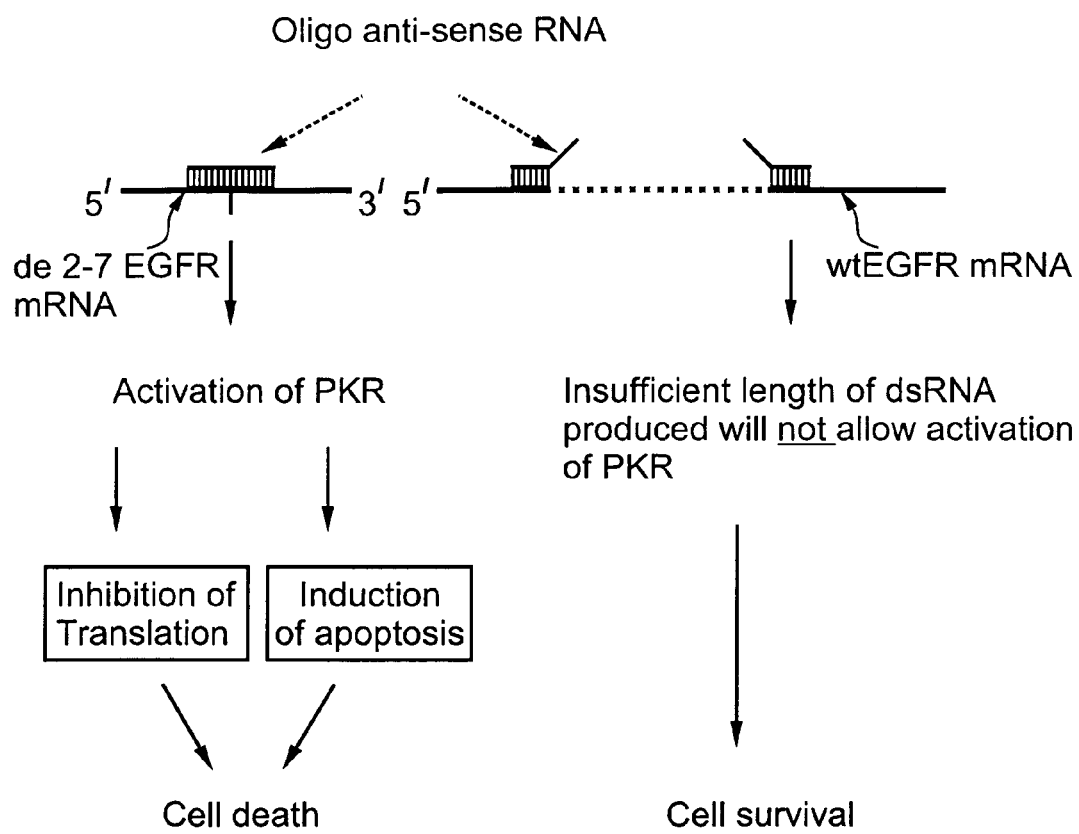
FIG. 1 shows the mechanism of specific activation of PKR in U87MGΔEGFR cells.

Embodiments of the invention are directed to selectively killing target cells. For clarification, terms have been defined for use in the description and the claims except where the context requires otherwise. Accordingly, "target cells" are defined as any cell involved in a pathologic condition that has an identified mutation even where the expression product of the mutated site is unknown. Examples of target cells are cancer cells more particularly neoplastic cells and metastasizing cells. Additional examples of target cells that are associated with disease in animals (including humans) include: skin cells in psoriasis and keloid scarring; vascular disorders including atherosclerosis and restenosis; vasculogenesis and angiogenesis, for example diabetic retinopathy. Target cells may include infectious agents including eukaryotic organisms, for example; protozoa and mycoplasma. Additionally, target cells may include selected cells of the immune system, for example, autoimmune T-lymphocytes.

The neoplastic cells of many cancers have acquired chromosomal translocations and deletions. (See Table 1) Such chromosomal rearrangements and truncations lead to the production of unique mRNA species which are the result of alternative splicing of pre-mRNA. Some genes express as a single truncated form of mRNA or mRNAs formed when two genes are fused after translocation. The term "single transcript" or "unique transcript" may be defined as a contiguous sequence associated with a mutation in contrast to two or more smaller transcripts that arise in the absence of a mutation.

The term "antisense RNA" includes any oligonucleotide that is capable of hybridizing to mRNA in the target cell and triggering double stranded RNA dependent protein kinase. The oligonucleotide may be a chimera between RNA and DNA. The oligonucleotide may be modified in the base moiety, the sugar moiety or the phosphate backbone for example, to improve its stability. The oligonucleotide may include appended groups such as peptides or agents facilitating transfer across membranes. Examples of modified nucleotides include thos known in the art, examples of which are provided in U.S. Pat. No. 5,955,306 herein incorporated by reference.

Selective killing of cells is achieved by activating double stranded RNA dependent protein kinase (PKR) through the formation of double stranded RNA of sufficient length to activate the enzyme only in cells with a mutation. In a preferred embodiment, this is achieved by introducing at least one anti-sense oligonucleotide into a population of cells either in vitro or in vivo by any method known in the art. This includes the use of vectors such as plasmids, DNA or RNA virus vectors, liposome encapsulated nucleic acids or naked DNA. Examples of DNA virus vectors include but are not limited to vaccinia virus, herpes virus and adenovirus vectors. Examples of RNA virus vectors include retroviruses including lentiviruses. The virus vectors may be engineered to achieve an infection efficiency of up to 100% (see Examples 1 and 6). Alternatively, the nucleic acid may be administered within a hydrophilic excipient material (U.S. Pat. No. 5,994, 314). The anti-sense RNA encoding sequences may be introduced into the host genome and stable expression of anti-sense RNA obtained. Expression of anti-sense RNA may be enhanced placing the anti-sense sequence under inducible or consitutive strong promoters, for example the U6 small nuclear RNA promoter. Early transcription termination signals in the anti-sense RNA are avoided or removed. The nucleic acid may be but is not required to be specifically targeted to selected cells because the mode of action is such that only targeted cells will form double stranded RNA of sufficient length to activate PKR.

Replicated anti-sense RNA reagent, produced after transfection or infection of target and non-target cells and target cells or target cells only, hybridizes substantially completely with mRNA transcribed from a pre-selected genetic locus in the target cells. The replicated anti-sense RNA may be a single full length molecule or alternatively may be more than one smaller anti-sense molecules which nonetheless collectively hybridize to messenger RNA in the target cell to form a single double stranded (ds) molecule. The messenger RNA is transcribed from a genetic locus that differs in sequence from the equivalent locus in non-target cells by a mutation in the sequence. A mutation is defined here as any of a substitution, a translocation, a deletion or insertion, and a rearrangement where one or more bases are involved. The intact double stranded RNA formed by hybridization of anti-sense RNA and messenger RNA in the target cells is of a length suited for activating PKR and bringing about cell death. The length of double stranded RNA suitable for activating PKR is at least 30 nucleotides, and generally less than 120 nucleotides in size, more particularly less than 100 nucleotides with an improved effect when the length is between 35 and 80 nucleotides. In non-target cells, the length of dsRNA produced upon hybridization is insufficient to activate PKR because the complementary region is not contiguous in the presence of non mutated sequence. Consequently, cell death is not triggered by PKR in those cells.

FIG. 1 is a diagrammatic representation of how anti-sense RNA fragments may hybridize to messenger RNA to form a contiguous double stranded sequence of 30-85 nucleotides in the target cells so as to give rise to the inhibition of translation and to aptoptosis. In contrast, in wild type cells, the anti-sense RNA fragments hybridize to messenger RNA at distant sites and therefore produce two distinct and substantially shorter double stranded RNA molecules. These short fragments do not effectively activate PKR in non-target cells and therefore cell death is not triggered in these cells. To identify cancer cells having a mutation which may be used to activate PKR and thereby give rise to apoptosis, the expression of PKR and PKR activity status may be examined prior to the implementation of the dsRNA killing strategy ("DKS"). In order to implement DKS, any unique mRNA molecule may be targeted with a vector containing complementary nucleotide sequences or with naked oligonucleotides, including those sequences which lack a defined function. The dsRNA is generated in situ following a binding event between the oligonucleotides introduced into the cell or made in the cells from template introduced into the cell:

The pharmaceutical composition for administering the oligonucleotides may be formulated using one or more physiologically acceptable carriers or excipients depending on the route of administration. It is envisaged that the pharmaceutical composition may be administered by any technique known in the art including oral administration, administration by injection, transdermal administration or administration through the mucosal surface. Examples of formulations that may be used are provided in U.S. Pat. No. 5,955,306 incorporated by reference.

Thus the approach described here is applicable to the treatment of a wide range of cancers and other proliferative disorders in which chromosomal translocation and truncation mutations occur (Table 1). Support for the general approach described in FIG. 1 is provided in the examples which are discussed below. The examples are not intended to be limiting.

In an embodiment of the invention, an interferon was added to further enhance the activation of dsRNA dependent protein kinase in the presence of double stranded RNA (Example 5). Whereas any interferon can be used, the enhancement effect is exemplified using alpha interferon. This approach may be used in the treatment of cell proliferative disorders in subjects including neoplastic disorders exemplified in Table 1.

In certain embodiments of the invention, the homology of antisense RNA for mRNA may be determined in vitro under stringent conditions of hybridization. The stringent conditions for hybridization include those that are generally accepted in the art such as described in chapter 6 of "A Compendium of Methods from Current Protocols in Molecular Biology" 1992 ed. Asubel et al. pub. John Wiley & Sons, Inc. Alternatively, effective hybridization is determined in situ between antisense RNA and mRNA as determined by a biological assay in which PKR activity is measured.

In a preferred embodiment of the invention, a pharmaceutical composition for treating proliferative disorders is provided that utilizes a vector or naked DNA to generate antisense RNA in the target cell for binding messenger RNA so as to cause double stranded DNA of sufficient length to be formed and to activate PKR and bring about cell death. The composition may be administered in a pharmaceutically acceptable non-toxic formulation suited for providing access to the target cells and minimizing breakdown of the composition either in storage or incurred during administration. This formulation may include encapulation within liposomes or absorption to microbeads. The composition may also be modified to provide an effective clearance profile in the subject. The composition may be administered by any one of a number of routes including transdermally, orally, or by intravenous, intramuscular or transmucosal means. It may be in liquid form and as a spray. An effective amount of an antisense RNA is defined to be sufficient to cause cell death to a significant number of target cells so as to be beneficial to the patient with respect to disease outcome or symptom alleviation. The pharmaceutical composition may include additional agents to enhance the therapeutic effect of the formulation so as to enhance activation of double stranded RNA dependent protein kinase and subsequent cell death.

Embodiments of the invention are exemplified by lymphomas. A number of recurring cytogenenetic abnormalities have been identified in various lymphomas. These abnormalities have been found to correlate with clinical, morphological and immunophenotypic characteristics (reviewed in Ong and Beau, 1998 Seminars in Oncology 25: 447-460). For example, in 70%-80% of human follicular lymphoma (FL) cases, a non-Hodgkin's lymphoma subtype is characterized by a t(14;18) chromosomal translocation that joins the 3' non-coding region of the antiapoptotic gene bcl-2 and the immunoglobulin heavy chain locus (bcl-2/IgH) (Tsujimoto et al., 1984; Bakhshi et al., 1985). As a result, these lymphomas express elevated levels of both bcl-2/IgH chimeric transcript and Bcl-2 protein (Cleary et al., 1986, Cell 47: 19-28) which possess survival advantages associated with neoplastic transformation (Cory, 1986: Advance in Cancer Research 47: 19-28). Another lymphoma subtype is large anaplastic transformation (ALCL). More than half of these lymphomas possess the chromosomal translocation t(2:5), that leads to the expression of a fusion protein comprised of the amino-terminal portion of the nuclear phosphoprotein nucleophosmin (NPM) and the cytoplasmatic domain of anaplastic lymphoma kinase (ALK) (Morris et al., 1994 Science 263: 1281-1281).

In another example, glioblastomas have mutations arising from deletions and translocations. Examples 1-6 describe how antisense RNA can give rise to double stranded RNA which activates PKR bringing about apoptosis in target cells.

TABLE 1

Genetic Abnormalities in Cancers

| Phenotype | Rearrangement | Involved Genes | Reference |
|---|---|---|---|
| B-cell NHL | | | |
| BL | t(8; 14)(q24; q32) | MYC, IGH | Ong et al. Semin. Oncol 1998; vol 25: 447-60 |
| | t(2; 8)(p12; q24) | IGK, MYC | |
| | t(8; 22)(q24; q11) | MYC, IGL | |
| FL, DCLL | t(14; 18)(q32; q21) | IGH, BCL2 | Ong et al. |
| DLCL | t(3:22)(q27; q11) | BCL6, IGL | Ong et al. |
| | t(3; 22)(q27; q32) | BCL6, IGL | |
| | t(3q27) | BCL6 | |
| MCL | t(11; 14)(q13; q32) | CCND I, IGH | Ong et al. |
| LPL | t(9; 14)(p13; q32) | PAX5, IGH | Ong et al. |
| SLL | t(14; 19)(q32'q13.3) | IGH, BCL3 | Ong et al. |
| MALT | t(11; 18)(q21; q21) | | Ong et al. |
| Variable | t(1; 14)(p22; q32) | LYT10, IGH | Ong et al. |
| | t(1; 14)(q22; q32) | RCK, IGH | |
| | t(3; 14)(p21; q32) | LPC, IGH | |
| | t(10; 14)(q24; q32) | | |
| | t(11; 14)(q23; q32) | | |
| | t(11; 14)(q23; q32) | | |
| T-cell NHL | | | |
| ALCL (CD30+) | t(2; 5)(p23; q35) | ALK, NPM | Ong et al. |
| CTCL | r(10q24) | LYT10 | Ong et al. |
| Variable | t(7; 14)(q35; q11) | TCRB, TCRA | Ong et al. |
| | t(11; 14)(p13; q11) | RBTN2, TCRD | |
| | inv(14)(q11q32) | TCRA, TCL I | |
| | t(14; 14)(q11; q32) | | |
| Leukemia | | | |
| CML | t(9; 22) | BCR, ABL | Shtivelman et al. Nature 1985; 315: 550.4 |
| AML | t(7; 11)(p15; p15) | NYP98, HOXA9 | Kwong et al. Genes-Chromosome-Cancer 1999; 25: 70-4 |
| Other Cancers | | | |
| Multiple liposarcoma | t(12; 16)(q13; p11) | TLS/FUS, CHOP | Schneier-Stock, etal. Cancer-Gene-Vytogenet 1999; 111: 130-3 |
| Clear cell sarcoma | t(12; 22)(q13; q12) | EWS, ATFI | Pellin, et al. Genes-Chromosomes-Cancer, 1998; 23: 358-60 |
| DSRCT | t(11; 22) | EWS, WT1 | Shimizu, et al. Cancer-Genet-Cytogenet. 1998; 106: 156-8 |
| Synovial sarcoma | t(X; 18)(p11; q11) | SYT-SSX1 | Kawai et al. N. Engl. J. Med. 1998; 338: 153-60 |
| Thyroid cancer | PTC5 | RET, RFG5 | Klugbauer et al. Cancer-Res. 1998; 58(2): 198-203 |
| Neuroblastoma, Ewing cancers | t(11.22)(q24.q12) | EWS, FLI1 | Burchill, et al. Eur. J. Cancer. 1997; 33(2): 239-43 |
| Myoxoid chondrosarcoma | t(9; 22)(q22; q12) | EWS, TEC | Brody, et al. Am. J. Pathol. 1997; 150(3): 1049-58 |
| Alveolar rhabodomyosarcoma | 13q with either 2q35 or 1p36 | FKHR, PAX7/PAX3 | Weber-Hall, et al. Genes-Chromosomes-Cancer. 1996; 17(1): 7-13 |
| Prostate carcinoma | t(6; 16)(p21; q22) | TPC/HPR | Veronese et al. Cancer-Res. 1996; 56(4): 728-32 |
| Gastric carcinoma | 11q23 | Duplication of ALL-1 | Baffa et al. Proc. Natl. Acad. Sci, USA. 1995; 92(11): 4922-6 |
| Lung cancer | 3p21.3 | Alternative splicing of RBM6 | Timmer et al. Eur. J. Hum. Genet. 1999; 7(4): 478-86 |

TABLE 1-continued

Genetic Abnormalities in Cancers

| Phenotype | Rearrangement | Involved Genes | Reference |
|---|---|---|---|
| Breast and ovarian cancers | | Alternative splicing of TSG101 | Carney et al. J. Soc. Gynecol. Investig. 1998; 5(5): 281-5 |
| Pancreatic carcinoma | 3p14 | Alternative splicing of FHIT | Simon et al. Cancer Res 1998; 58(8): 1583-7 |
| Colorectal cancer | | Alternative splicing of hMSH2 | Xia et al. Cancer Res 1996; 56(10): 2289-92 |
| Wilms', kidney and thyroid tumors | | Alternative splicing of PAX8 | Poleev et al. Eur J Biochem 1995; 228(3): 899-911 |
| Retinoblastoma | | Deletion of RB | Hashimoto et al. Onocogene 1991; 6(3): 463-9 |
| Glioblastoma | | Deletion of EGFR | Sugawa et al. Proc. Natl. Acd. Sci. U.S.A. 1990; 87(21): 8602-6 |

1. References indicate fusion of specified genes.
2. Abbreviations: NHL non-Hodgkin's lymphoma; BL Burkitt's lymphoma; FL follicular lymphoma; DLCL diffuse large cell lymphoma; MCL mande cell lymphoma; LPL lymphoplasmacytoid lymphoma; SLL small lymphocytic lymphoma; MALT mucosa associated lymphoid tissue; ALCL anaplastic large cell lymphoma; CTCL cutaneous T cell lymphoma; DSRCT desmoplastic small round cell tumor; CML chronic myeloid leukemia; AML acute myeloid leukemia.

The references in Table 1 describe published data on mutations for certain malignancies. The locations of the mutations and their sequences are readily accessible to the person of ordinary skill in the art through publicly available databases. Those sites provided in Table 1 are given as examples. The invention is not intended to be limited by these examples. Exemplary sequences associated with selected deletions described in Table 1 are provided below (AS RNA denotes anti-sense RNA and "Translocation" refers to the mutation on the DNA).

```
FL,DCLL T(14, 18) (Q32; Q21) IGH,BCL2
SEQ ID No 1:
3'-GUUUUCCUAAGACUCUUCCACUCUAUUCUUGACUCA-5'
AS-RNA (36 bases)

SEQ ID No 2:
5'-CAAAAGCATTCTGAGAAGGTGAGATAAGAACTGAGT-3'
Translocation

LPL T(9; 14) (P13; Q32) PAX5, IGH
SEQ ID No 3:
3'-ACUUAAAAUAAAAAAAACUUCCCCUGAAUCACUACAGACA
AS-RNA (40 bases)

SEQ ID No 4:
5'-TGAATTTTATTTTTTTTGAAGGGGTCTTAGTGATGTCTGA
Translocation

ALCL (CD30+) T(2; 5) (P23; Q35) ALK, NPM
SEQ ID No 5:
3'-CUGUUAACUACUGGACCUUCACAUGGCGGCCUUCGUGGUC
AS-RNA (40 bases)

SEQ ID No 6:
5'-GACAATTGATGACCTGGAAGTGTACCGCCGGAAGCACCAG
Translocation

Glioblastoma Deletion in EGFR
SEQ ID No 7:
3'-CCGAGACCUCCUUUUCUUUCCAUUAAUAdACCACUGUCUA
AS-RNA (40 bases)

SEQ ID No 8
5'-GGCTCTGGAGGAAAAGAAAGGTAATTATGTGGTGACAGAT
Translocation
```

The detection of these and other recurring abnormalities are useful for diagnosis and prognosis assessment leading to treatment with anti-sense RNA to trigger cell death.

EXAMPLES

Example 1

Targeted Cell Killing of Glioblastoma Cells

Formation of Plasmids for Transfection into Target Cells.

Figure 2:
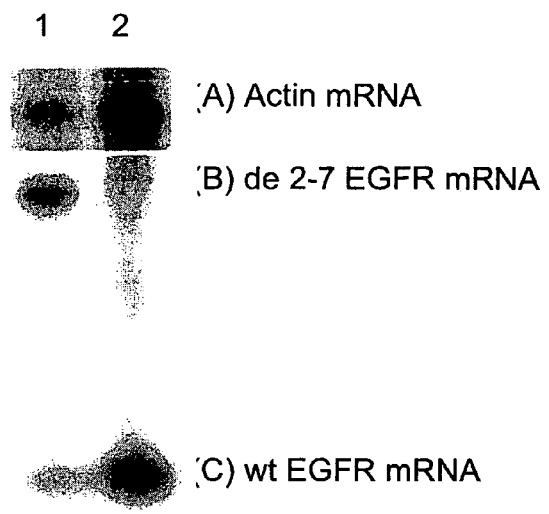
FIG. 2 shows the expression of EGFR mRNA in glioblastoma cells analyzed by RNAse protection analysis. Expression of mutant and wild type forms of EGFR mRNA in U87MGΔEGFR (1) and U87MG (2) are demonstrated using RNase protection analysis. The bands on the gel correspond in descending order to (A) actin mRNA; (B) Δ2-7 EGFR mRNA and (C) wt EGFR mRNA.

The U87MGΔEGFR cell line (Nishikawa R et al.; (1994) Proc. Natl. Acad. Sci. USA 91: 7727-31) which was created by infection of human glioblastoma cells U87MG with amphotropic virus carrying EGFR gene deleted for exons 2-7, expresses truncated form of EGFR (Δ2-7EGFR) and the U87MG cell line (Ponten J., et al., (1968) Pathol. Microbio. 'I Scand.; 74:465-86) expresses wild type (wt) form of EGFR. This was determined by RNase Protection Analysis that showed expression of wild type EGFR mRNA in both U87MG (parental) and U87MGΔEGFR cells, while mutant mRNA was expressed only in U87MGΔEGFR cell line (FIG. 1). The level of mutant mRNA was several times higher than wt mRNA. The amount of wt mRNA (U87MG) to mutant mRNA (U87MGΔEGFR) was determined with respect to levels of actin in each sample. (FIG. 2). These cell lines provided a suitable model system to determine whether PKR could be selectively activated in target cells as schematically represented in FIG. 1.

Anti-Sense RNA Expressing Plasmid

To generate high levels of anti-sense RNA in the cell, the EGFR anti-sense sequence was cloned into a U6 expressing construct (He et al. (1998) J. Natl. Cancer. Inst.: 1080). In this construct, a U6 small nuclear RNA promoter controls expression of the subcloned gene by RNA polymerase III.

Figure 5:
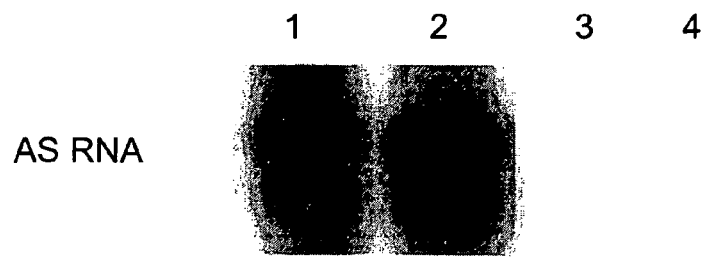
FIG. 5 shows the expression of anti-sense RNA in glioblastoma cells (1) transfected U87MGΔEGFR (2) transfected U87MG. (3) untransfected U87MGΔEGFR and (4) untransfected U87MG where both (1) and (2) were transfected with pΔEGFR-AS plasmid Expression of anti-sense RNA was detected by RNase protection analysis.

The Δ2-7 EGFR mRNA has a deletion of 801 nucleotide (nt) of the coding sequence of the extracellular domain (Kawai, A. et al. (1998) J. Med. 338: 153-60). This mutant is the most virulent form of glioblastoma. It is capable of expressing anti-sense RNA that is complimentary to short fragments of EGFR mRNA flanking the deletion region. (FIG. 5 shows the expression of AS RNA in glioblastoma cells). The AS RNA completely hybridizes with Δ2-7 EGFR mRNA yielding a double stranded molecule that is of sufficient length to activate PKR. In contrast, wild type EGFR mRNA undergoes hybridization with only half of the AS RNA yielding dsRNA with insufficient length to activate PKR. Once activated PKR was found to selectively inhibit growth of U87MGΔEGFR cells.

The Oligonucleotides

Figure 4:
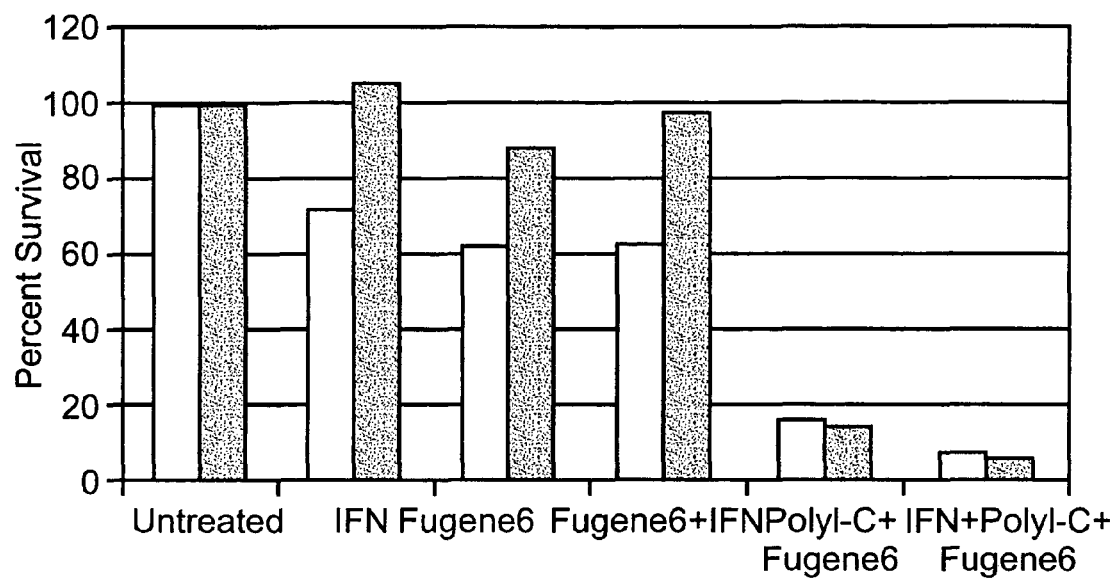
FIG. 4 demonstrates the effect of dsRNA on survival of glioblastoma cells. U87MG cells (white) and U87MGΔEGFR cells (black). Cells were transfected with polyI-C as indicated in the presence or absence of α-interferon and the controls were untreated cells

Vectors were constructed for expression of 39-bp long anti-sense and sense oligonucleotides corresponding to fragments of Δ2-7 EGFR mRNA flanking the deletion region. These vectors were synthesized and cloned into Xho I and Nsi I sites of the U6 expression plasmid. In this construct, the U6 small nuclear RNA promoter controls transcription of the subcloned gene by RNA polymerase III, generating high levels of short RNA. The anti-sense transcript is complementary to short fragments of mutant EGFR mRNA flanking the deletion region. Plasmid pΔEGFR was designed so that complete hybridization of the AS RNA with Δ(2-7) EGFR mRNA would yield a double stranded molecule with sufficient length to activate PKR. The expression of anti-sense RNA was tested by RNase Protection Analysis following transfection of the cells (FIG. 4). Sequences of the inserts are as listed below and were verified by sequence analysis.

```
                                         SEQ ID No 9
pAEGFR-AS:  TCTGTCACCACATAATTACCTTTCgTTTCCTCCAGAGCC

SEQ ID No 10
pAEGFR-S:   GCTCTGGAGGAAAAGAAAGGTAATTATGTGGTGACAGAT
```

The transcription termination signal for RNA polymerase III is a string of 4 or more thymidine residues (He et al. (1997) Cancer Res. 57:3993-9). To prevent early termination of transcription, thymidine in position 25 of pΔEGFR-AS was replaced for guanine (bold). Since it was shown that binding and activation of PKR by dsRNA can tolerate mismatch of single pair of nucleotides (Kunkel et al. (1989) Nucleic Acid Research, 17:7371-9), this replacement did not interfere with PKR activation. A 39 nt oligonucleotide was utilized in preference to a 40 nt to avoid producing a transcript having an extra sequence of Xho I site that could hybridize with wt EGFR mRNA generating a dsRNA with 24 bp length. A dsRNA of 24 bp is potentially capable of activating PKR which would compromise the selectivity of the PKR for target cells.

Example 2

Transfection of Cell Lines With Plasmids

The cells of human glioblastoma line U87MG (Ponten et al. (1968) Acta Pathol. Microbio.' I Scand, 74: 465-86) which express wild type EGFR only were maintained in Dulbecco's modification of Eagle medium (DMEM) (Beith-Ha-Emek, Israel) supplemented with 10% fetal calf serum and antibiotics. The cells of U87MGΔEGFR line (Nishikawa et al. (1994) Proc. Natl. Acad. Sci. USA, 87:8602-6), which express both wild type and truncated form of EGFR were maintained in the same conditions plus 400 kg of G418 per ml were added to the medium.

Transfections either of DNA or dsRNA (polyI-polyC (polyI-C), Pharmacia) were performed using FuGene 6 Transfection Reagent (Boehringer Mannheim) according to manufacturer's instructions. Average transfection efficiency was determined as 30% by transfection of β-galactosidase encoding plasmid and subsequent β-galactosidase staining of the cells. Alternatively, U87MG and U87MGΔEGFR cells seeded in 96 well dishes at a density of 2000 cells/well were transfected three times at 48 hour intervals with pΔEGFR-AS/S plasmids (0.1 μg) and treated continuously with IFN-α (100 U/ml) to determine effect on cell growth (FIGS. 6a-b).

Figure 6A:
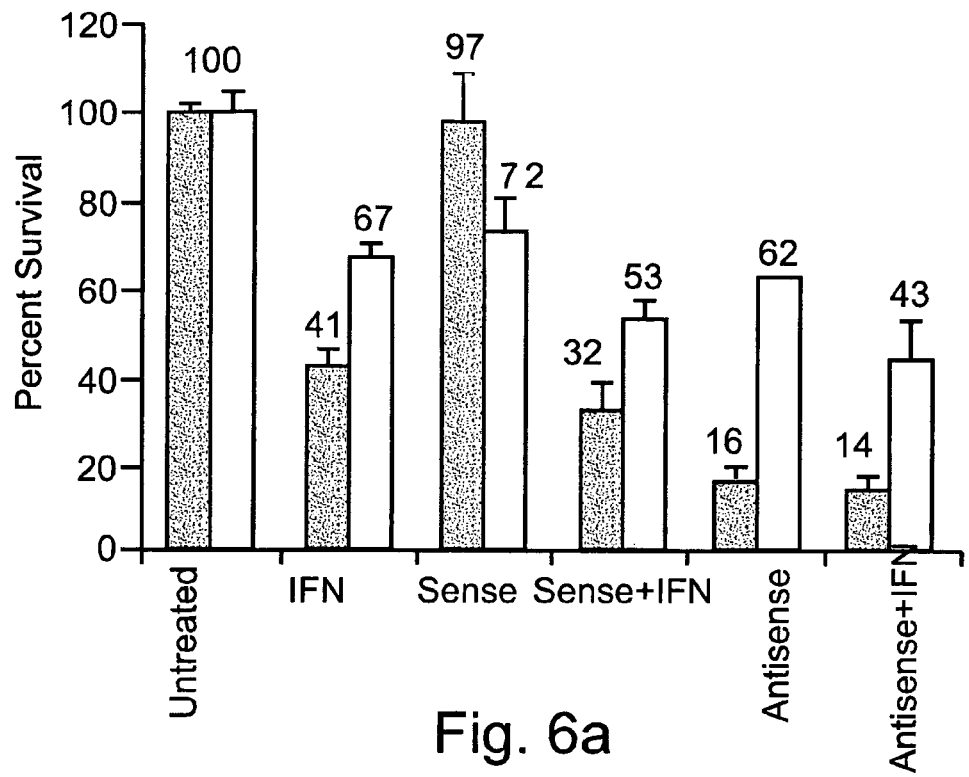
FIGS. 6a-b shows the effect of transfecting glioblastoma cells three times with anti-sense RNA expressing plasmid as measured by percent survival of cells.
Figure 6B:
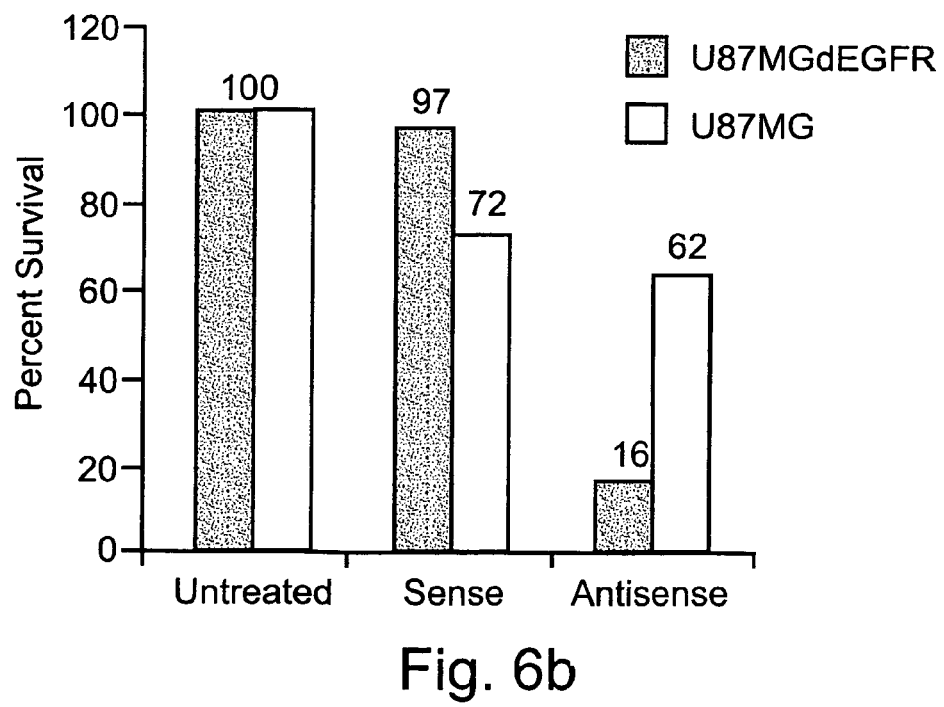

Transfection with pΔEGFR-AS into U87MGΔEGFR cells resulted in only 16% survival compared to the untreated cells, while effect on survival of U87MG cells was much less dramatic and is comparable to effect of transfection with pAEGFR-S (62 and 72% respectively) (see FIGS. 6a-b).

Figure 7:
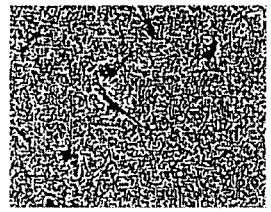
FIG. 7 shows the effect on glioblastoma cells (U87MGΔEGFR cells and U87MG cells) of transfection with anti-sense RNA expressing plasmids as visualized by light microscopy.
Figure 7:
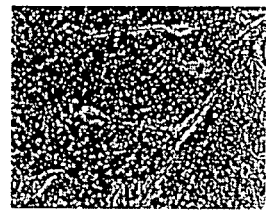
Figure 7:
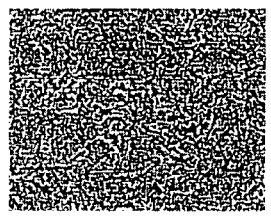
Figure 7:
Figure 7:
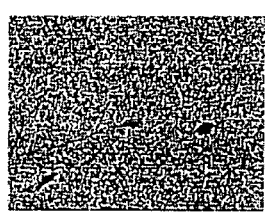
Figure 7:
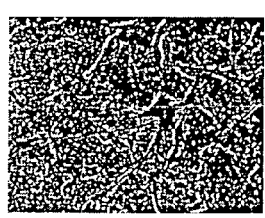
Figure 7:
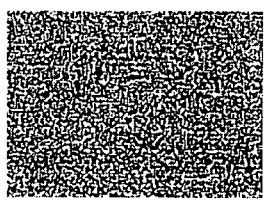
Figure 7:
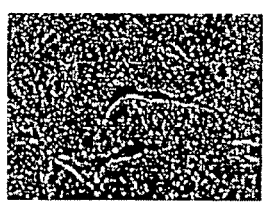
Figure 7:
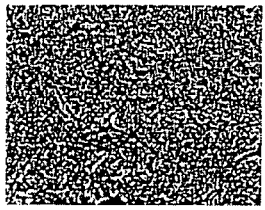
Figure 7:
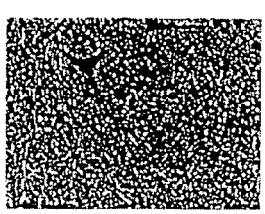
Figure 7:
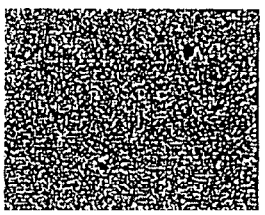
Figure 7:
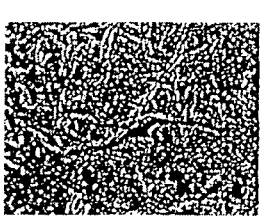
Figure 9:
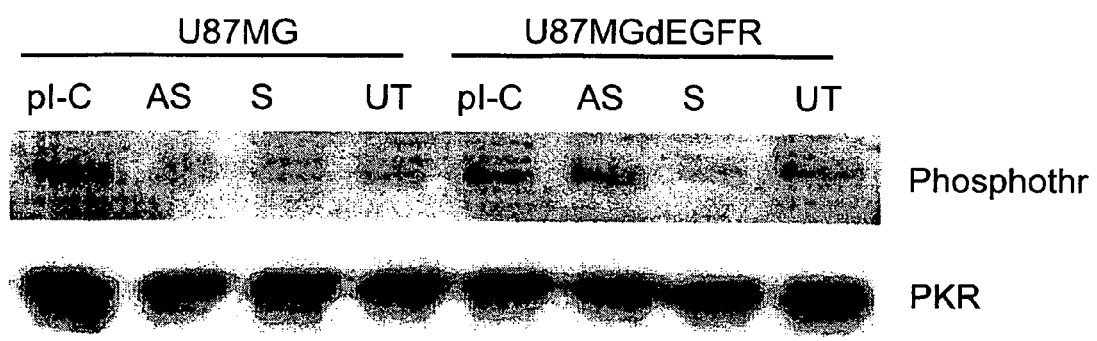
FIG. 9 shows activation of PKR in glioblastoma cells treated with 500 U/ml of IFN-α by Western blot analysis of lyzed cells. (UT) untreated cells; p-IC cells transfected with PolyI-PolyC; (AS) pΔEGFR-AS; (S) pΔEGFR-S. (AS=antisense, S=sense)

Transfection efficiency was evaluated by co-transfecting cells at a density of 10,000 cells/well in a 24 well plate with pΔEGFR-AS/S plasmids (1.5 μg of each) containing β-galactosidase coding sequences, growing overnight and staining the cells with 0.5 μg β-galactosidase. The results of this experiment captured by digital camera on a microscope were in good agreement with the results of triple transfections pΔEGFR-AS to glioblastoma cells showing the strong effect of anti-sense RNA on U87MGΔEGFR cells and virtually no effect on U87MG cells (FIG. 7).

To increase transfection efficiencies of the plasmids (single transfection efficiency-30%), antisense/sense RNA expressing lentiviral vectors with high infection efficiency (100%) were constructed. These viral vectors may also be in gene therapy of human subjects. For lentiviral vector production, the U6 cassette was excised from pΔEGFR-AS/S by BamHI/EcoRI digestion, filled in and ligated with SIN-PGK transfer vector (Zufferey, R. et al. (1987) Nat. Biotechnol., 15:871-5) which was digested with XhoI and filled in. Clones with insert orientation that preserves the same direction of the transcription from 5'LTR of the plasmid and the U6 promoter were selected. Virus was obtained by transient co-transfection of the constructed plasmids with pMD.G and pCMVDR8.91 plasmids into the 293T cell line (Zufferey et al. (1997); Naldini, L., (1996) Science 272:263-7). The expression of anti-sense and sense RNA was verified by RNase protection analysis following infection of the cells.

Figure 10A:
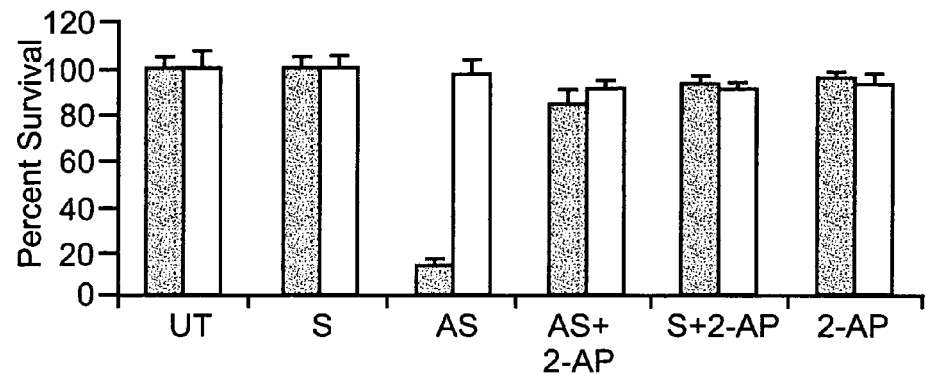
FIG. 10 shows the effect of pΔEGFR-ASRNA on growth of glioma cells (a) effect of infection of pΔEGFR-ASRNA expressing vector on growth of glioma cells in a monolayer. Percentage surviving cells was calculated relative to untreated cells (UT); (b) effect of pΔEGFR-ASRNA on growth of glioma cells in soft agar.
Figure 10B:
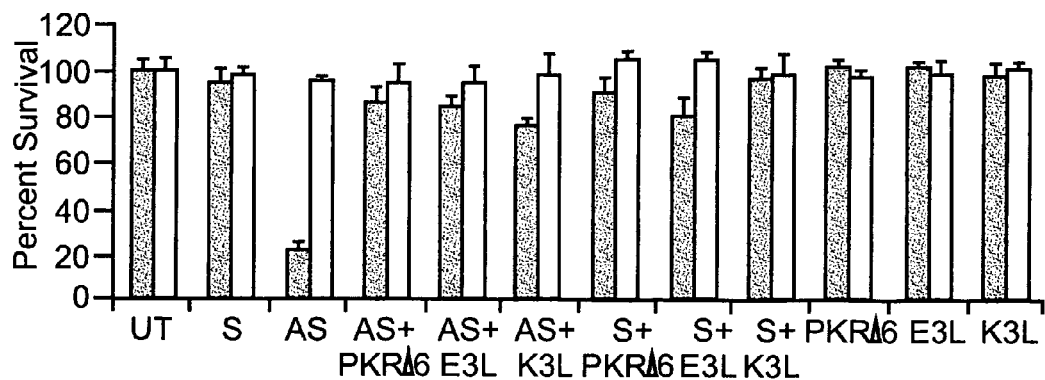

Single infection of the antisense expressing vector resulted in the death of more than 90% of U87MGΔEGFR cells grown in monolayer while no significant effect was observed on either U87MG cells or U87MG cells over-expressing the wild type EGFR (FIG. 10a). A similar effect was observed on cells grown in soft agar (FIG. 10b). Growth inhibition did not result from the reduction in expression of truncated EGFR since this receptor does not enhance proliferation of the cells grown in vitro.

Example 3

Detection of mRNA Levels in Cells

Messenger RNA levels were measured by RNase protection analysis. Human glioblastoma cells were seeded at a density of 1×10⁶ per 6-cm diameter petri dish and grown overnight and transfected with two μg of either pΔEGFR-AS or pΔEGFR-S containing plasmid using Fugene 6 Transfection Reagent (Boehringer Mannheim). Total RNA was isolated from either transfected and untransfected cells at 24 hours after transfection using RNA Pure System (Boehringer Mannheim) according to the manufacturer's instructions. 10 μg of RNA were hybridized with appropriated probe and RNase protection analysis was performed using RPA II Kit (Ambion Inc., USA) according to manufacturer's instructions.

Hybridization probes were prepared as follows: pΔEGFR-AS and pΔEGFR-S plasmids were digested with BamHI and riboprobes containing complementary sequences to either anti-sense or sense RNA were transcribed from SP6 promoter using Riboprobe System-SP6 (Promega). Riboprobe complementary to sense RNA was used to detect EGFR mRNAs levels in the cells. This probe protects one 39 nt fragment of mutant EGFR mRNA and two fragments (20 and 19 nt) of wild type EGFR mRNA, flanking the deletion region.

Effect of dEGFR Anti-Sense RNA on Protein Synthesis

PKR was demonstrated to be activated upon expression and hybridization of ΔEGFR anti-sense RNA with target mRNA so as to inhibit protein synthesis. Global translation levels were measured in infected and uninfected U87MG and U87MGΔEGFR glioblastoma cells as well as the translation efficiency of mutant EGFR mRNA after infection of the cells with anti-sense RNA vector and treatment with α-interferon.

The translation levels are determined by the ratio of total protein level to total mRNA level and the ratio of EGFR protein level to EGFR mRNA level in both mutant and wild type.

Determination of protein concentration was carried out as follows: Cells were lysed using 40 µl of Lysis buffer 1. 10 µl of lysates were then transferred to small pieces of Whatman blotting paper, as were BSA standards dissolved in the same buffer. The samples were stained with Coomassie blue for 30 min. using 30 ml of staining buffer (2.5 g/L of Coomassie brilliant blue G-250 (BDH), 40% methanol and 10% acetic acid). Samples were then extensively washed with washing buffer (1% glycerol, 20% methanol, 7% acetic acid) and transferred to 24 well plates. The color was extracted with 1 ml of 3% SDS. Duplicates of 200 µl of the obtained solutions were transferred to 96 well plate and the optical density was read in an ELISA reader at 595 nm. Concentration of the protein was calculated using BSA concentrations as a standard.

Example 4

Visualization of Stained Cells by Light Microscopy

Methylene blue staining of the cells: Cells were seeded into 96-wells plate and grown overnight. After appropriate treatment, cells were fixed with glutardehyde at 0.5% of final concentration. Cells were then washed three times with double distilled $H_2O$ and one time with 200 µl of Borate Buffer (0.1 M, pH 8.5). Cells were than stained with 200 ul of 1% Methylene Blue resolved in Borat Buffer. After intensive washing and drying, the color was extracted with 200 µl of 0.1 M HCl for one hour in 37° C. and the optical density was read in ELISA reader at 630 nm.

FIG. 8 shows the results of methylene blue staining of the cells performed 48 hours after the last transfection. Percent survival of the cells was calculated regarding to untreated cells. Graphs A and B depict the results of the same experiment where B does not include the effect of IFN-α. (FIG. 8)

Alternatively, cells were stained with β-galactosidase. Cells were seeded into 24 well at density of 10,000 cells per well and grown overnight. After appropriate treatment, cells were washed with PBS and fixed with Fixation Buffer (2% Formaldehyde, 0.2% Glutardehyde diluted in PBS) for 5 min. at 4° C. The cells were then washed twice with PBS and incubated overnight in 1 ml of Staining Buffer (1 mg/ml X-gal, 5 mM K-ferricyanide, 5 mM K-ferrocyanide, 2 mM $MgCl_2$ in PBS, pH7.4). The colored cells were detected by light microscopy.

Example 5

Measurement of PKR Expression

Cells were seeded at a density of $5 \times 10^5$ per 6-cm diameter petri dish and grown overnight. Cells were then infected with appropriate vector and treated with 2-aminopurine (Sigma) where indicated. PolyI-C (25 µg/ml) was transfected using FuGene6™ transfection reagent (Roche) 1 hour before lysis. Sixteen hours after infection cells were lysed with 200 µl of Lysis Buffer 1 (20 mM Tris-HCl pH 7.5, 5 mM $MgCl_2$, 50 mM KCl, 400 mM NaCl, 2 mM DTT, 20% Glycerol, 20 mM β-glycerophosphate, 100 mM NaF, 10 µg/ml PMSF, 10 µg/ml Aprotinin, 1% Triton X-100) and the samples were centrifuged at 12,000×g for 5 min. at 4° C. to remove cell debris. Fifty µg of each sample were taken for Western blot to determine phosphorylation of endogenous eIF-2α. For determination of PKR activity 80 µg of each sample were incubated for 20 min at 37° C. with 0.5 µg of recombinant eIF-2α (Sood, et al. (2000) Genetics. 154:787-801) in reaction buffer (20 mM Tris-HCl pH 7.5, 2 mM $MgCl_2$, 2 mM $MnCl_2$ 50 mM KCl, 5% Glycerol, 10 mM NaF, 100 mM ATP). Samples were then electrophoresed and blotted. The blots were then probed with either mouse monoclonal anti-PKR antibody (RiboGene, Inc.), rabbit polyclonal antibody against phosphorylated form of eIF-2α (Research Genetics, Inc), or goat polyclonal anti-eIF-2α antibody (Santa Cruz) using the ECL procedure as described (DuPont RENAISSANCE western blot chemiluminescence reagents). Anti-goat, anti-rabbit and anti-mouse antisera labeled with HRP were obtained from Jackson Immuno-Research Laboratories, Inc (Town, USA).

In the Presence of Interferon

Figure 3:
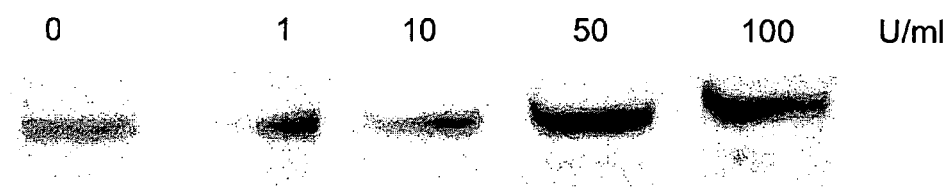
FIG. 3 shows the effect of IFN-α on expression of PKR in U87MGΔEGFR cells on Western blots. Cells were treated for 18 hours with varying concentrations of IFN-α and then lyzed. The gel shows the effect of adding 0, 1, 10, 50 and 100 U/ml of α-interferon.

The PKR/dsRNA ratio is important for the initial activation of PKR. IFN-α, which has already was tested clinically against glioblastomas (Jereb et al. Acta Oncol (1994) 33:651-4) induces expression of PKR in U87MGΔEGFR cell lines (FIG. 2). Indeed, treatment of transfected cells with IFNs, enhance expression of PKR expression. FIG. 3 shows the results of increasing concentration of IFN-α on expression of PKR in U87MGΔEGFR cell lines on Western blots.

Western Blot Analysis: Cells were seeded at a density of $1 \times 10^6$ per 6 cm diameter-petri dish and grown overnight. For determination of effect of IFN-α on PKR expression, cells were lysed in 300 µl of Lysis Buffer 1 (10% Glycerol, 0.05 M Tris-HCl pH-6.8, 5% β-mercaptoethanol, 3% SDS, 0.25% Bromphenol Blue, 100 µg/ml PMSF, 1 mg/ml Aprotinin) and boiled. Equal amounts of proteins were electrophoresed through 10% SDS PAGE. (FIG. 3). The separated proteins were then transferred to nitrocellulose membranes before being probed with rabbit polyclonal anti-PKR antibody (Santa Cruz) using ECL procedure as described (DuPont RENAISSANCE Western Blot Chemiluminescence reagents). Goat anti-rabbit and anti-mouse antiserums labeled with HRP were obtained from Jackson Immuno-Research Laboratories, Inc.

For determination of PKR activation, cells grown in the same conditions were transfected with either pΔEGFR-AS or pΔEGFR-S and treated with 500 U/ml of interferon (IFN-α) for 18 hours. PolyI-C was transfected 2 hours before lysis. Cells were then lysed with 500 µl of Lysis Buffer 2 (50 mM Tris-HCl pH 8.0, 150 MM NaCl, 0.02% Sodium Azide, 100 µg/ml PMSF, 1 mg/ml Aprotinin, 1% Triton X-100) and the samples were centrifuged at 12,000×g for 5 min at 4° C. to remove cell debris. PKR was immunoprecipitated with rabbit polyclonal anti-PKR antibody (Santa Cruz), electrophoresed and transferred to PVDF membranes (Millipore, Inc.). The blots were then probed with either mouse monoclonal antiphosphothreonine antibodies (Zymed Laboratories, Inc.), or polyclonal anti-PKR antibody using ECL procedure as described above. PKR concentration and phosphorylation were determined by scanning autoradiograms and measurement of optical density of each band by Macintosh NIH Image 1.61 software.

The above results are confirmed by transfecting cells with plasmids expressing β-galactoside in combination with pΔEGFR-AS and pΔEGFR-S plasmids. Cells were seeded into 24 well plates at a density of 10,000 per well and grown overnight. Cells were then transfected with 0.5 kg of β-galactosidase expressing plasmid with a combination of 1.5 μg pΔEGFR-AS or pΔEGFR-S plasmids and treated with 500 U/ml of IFN-α where indicated. β-galactosidase staining of the cells was then performed and stained cells were detected through a microscope connected to a digital camera. The results are shown in FIG. 7.

Measurement of PKR Expression and Cell Growth Using Poly I-C

Poly I-C is a synthetic dsRNA molecule with indefinite length which activates PKR both in vitro and in intact cells (Hunter et al. (1975) Biol. Chem., 250:409-17; Clemens et al. (1975) Proc. Natl. Acad. Sci. USA 72:1286-90; Farrell et al. (1977) Cell, 11:187-200; Levin et al. (1978) Proc Natl Acad Sci USA, 75:1121-5; Levin et al. (1980) Proc Natl Acad Sci USA, 77:832-6; Balachandran et al. (1998) EMBO J. 17:6888-902). As shown in FIG. 4, polyI-C has a strong effect on survival of both U87MGΔEGFR and U87MG cells leading to death of up to 84% of the cells. Treatment of the cells with IFN-α enhances the effect leading to 92% of cell death. Treatment of the U87MG cells with transfection reagent only (FuGene 6™) or transfection reagent in combination with IFN resulted in 38-39% cell death probably due to possible toxic effects of the reagent.

Effect of dEGFR Anti-Sense RNA on Induction of Apoptosis

Since it was shown that activated PKR is a strong pro-apoptotic protein, induction of apoptosis can be tested in both uninfected and anti-sense RNA expressing vector-infected U87MG and U87MGΔEGFR cells. Changes in expression of pro-apoptotic proteins are shown to be increased by activation of PKR.

Effect of Transfection of PKR Inhibitors on Survival of the Cells

To demonstrate that the death of the glioblastoma cells was caused by activation of PKR, it was shown that inhibitors of PKR could rescue the cells transfected with pΔEGFR-AS. Vaccinia PKR inhibitors (Davies et al. (1993) J. Virol; 67:1688-92) were selected for determining cell survival following PKR activation. In particular, the two vaccinia virus inhibitors of PKR-E3L and K3L, were used for the rescue experiment. The E3L gene of vaccinia virus encodes an inhibitor of the interferon-induced binding of double stranded RNA-dependent protein kinase to dsRNA. (Chang et al., (1992) Virology, 66: 1943-50.) The vaccinia virus K3L gene product potentiates translation by inhibiting double-stranded-RNA-activated protein kinase. This activity is thought to arise through the homology between K3L gene product and eIF-2α where the K3L gene product is an antagonist for binding with PKR (Davies et al. (1993) J. Virol., 67:1688-92).

Cells were seeded in 96 well plates at a density of 2000 cells per well and grown overnight. Cells were then transfected three times with 0.1 μg of appropriate plasmids. Interval times between transfections were 24 hours. Methylene blue staining was conducted 24 hours after the last transfection and percent survival of the cells was calculated with respect to untreated cells. FIG. 8 shows that co-transfection of plasmids encoding both inhibitors of PKR with pΔEGFR-AS, rescues the U87MGΔEGFR cells from death. Graphs A and B are results of the same experiment with B not showing effect of IFN-α.

Effects similar to the above with vaccinia virus proteins were observed when U87MGΔEGFR cells were infected with AS expressing vector and rescued with 2-aminopurine. The rescue by aminopurine further supports the involvement of PKR in cell death. Furthermore cotransfection of a plasmid encoding a transdominant negative mutant of PKR, PKRΔ6 with pΔEGFR-AS almost completely abrogated the effect of pΔEGFR-AS transfection alone.

Effect of ΔEGFR Anti-Sense RNA on Growth of U87MGΔEGFR Cells Injected to Mouse

To test the effect of ΔEGFR anti-sense RNA on cancer growth in in vivo conditions, U87MGΔEGFR cells are injected into mouse and the multiplication rate of the neoplastic cells is measured. Anti-sense RNA expressing vector is then introduced into the mice and the mice are further treated with IFN-α. The control consists of a group of mice that do not receive cancer cells but are infected with an anti-sense RNA expressing vector to test for possible side effects.

Example 6

PKR Involvement in Cell Killing

Figure 11A:
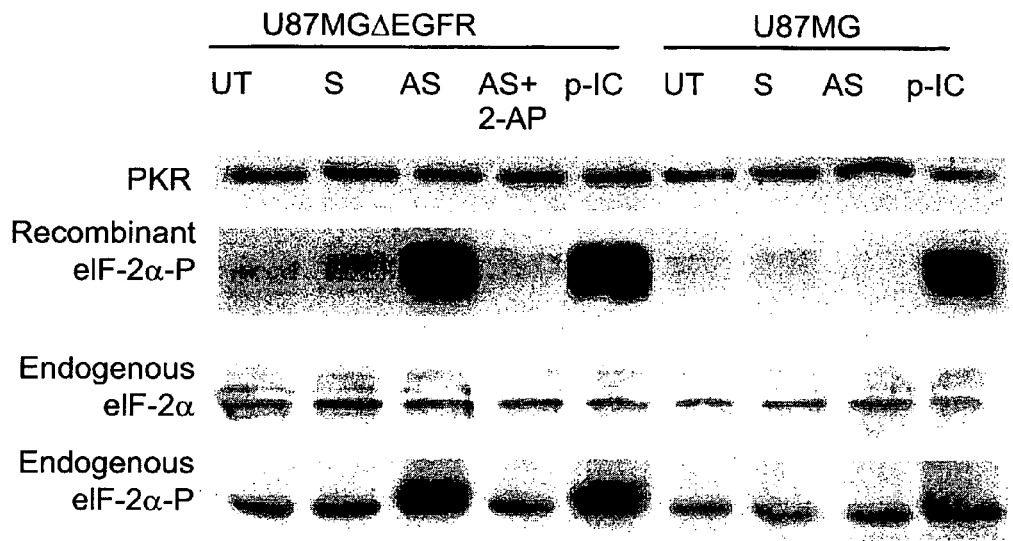
FIG. 11 shows (a) activation of PKR in glioblastoma cells. Cells either untreated (UT), transfected with pI-C, or infected with a vector and treated with 2-AP (5 mM final concentration) as indicated. (b) infection of AS RNA expressing vector on total translation in glioblastoma cells. The graph shows fold inhibition of total protein/total mRNA ratio with respect to untreated (UT) cells.
Figure 11B:
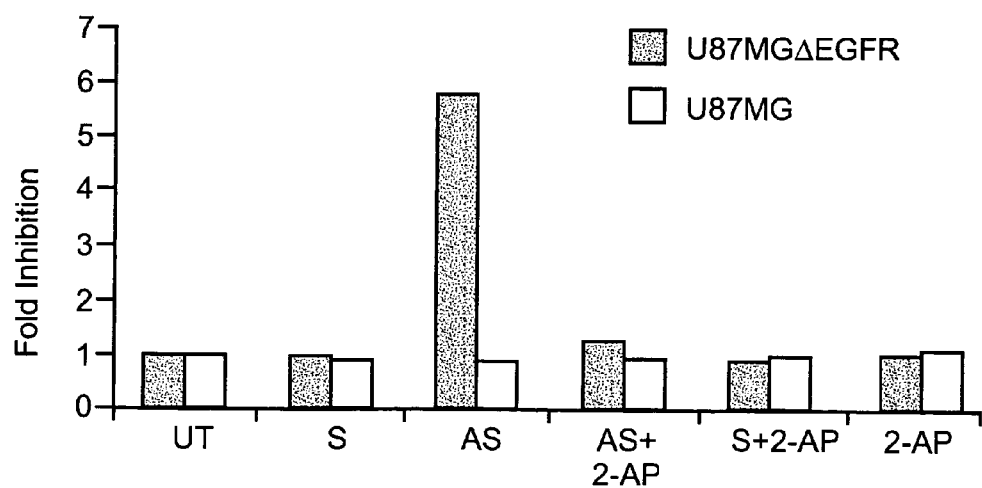

In order to examine PKR involvement in cell killing first the status of PKR activity was examined in the cells. In glioblastoma U87MG cells infected with anti-sense expressing vector PKR activation was identical either with sense infected or untreated cells (FIG. 10a). In contrast, infection of U87MGΔEGFR cells with AS RNA expressing vector led to strong PKR activation comparable with activation of PKR in cells transfected with the synthetic dsRNA molecule polyI-C. (FIG. 11a) PKR activation was completely inhibited in cells treated with the PKR inhibitor 2-aminopurine (2-AP). Infection of U87MGΔEGFR cells with AS RNA expressing vector also stimulated phosphorylation of endogenous eIF-2α while in U87MG cells phosphorylation of eIF-2α remained at the same level.

Figure 12A:
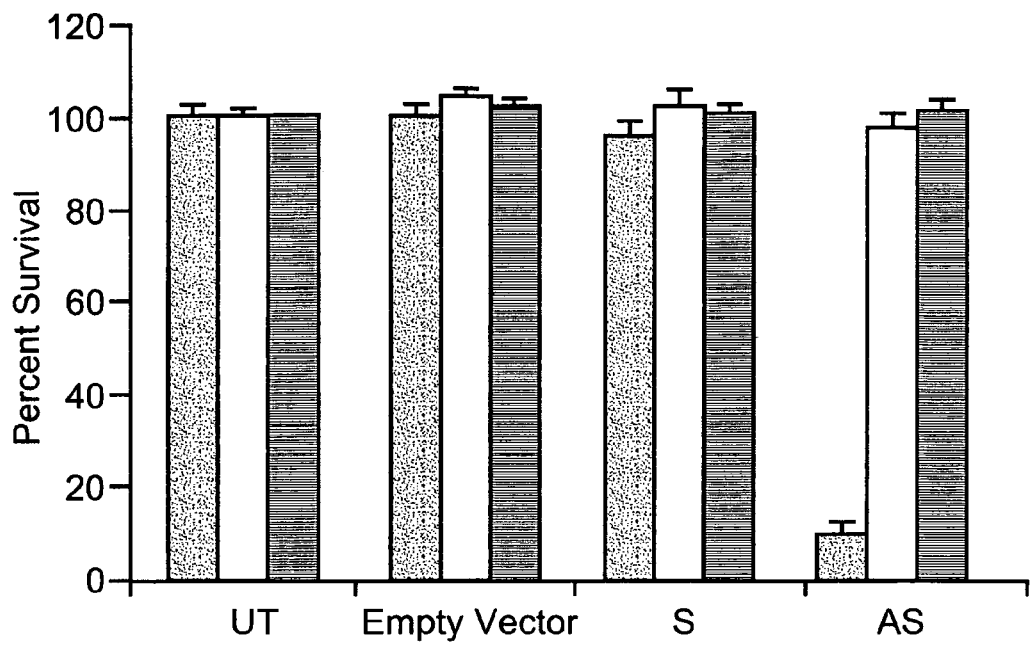
Figure 12B:
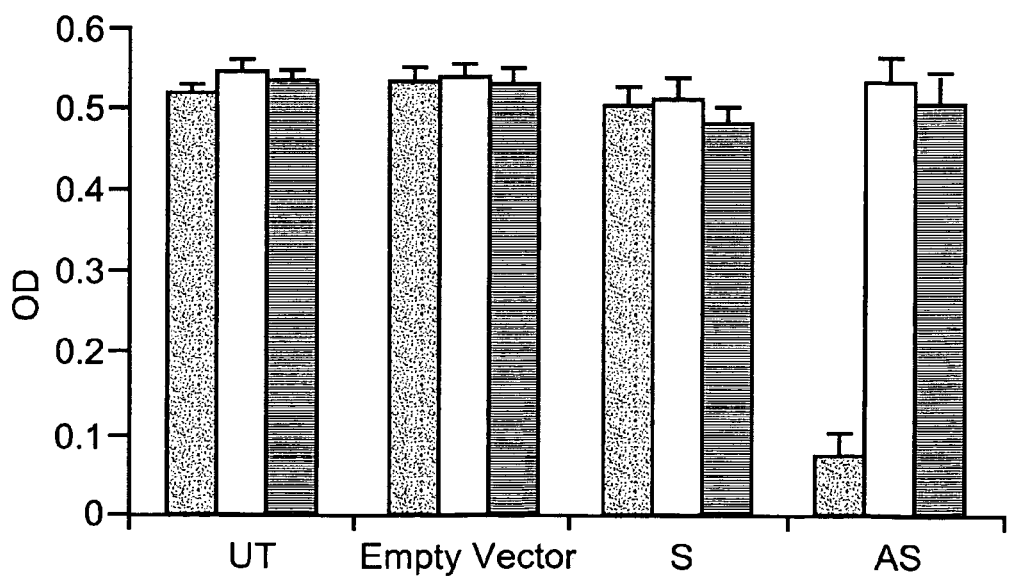

Next, whether the ΔEGRF-AS-induced activation of PKR does in fact lead to global inhibition of protein synthesis was examined. Infection of the U87MGΔEGFR cells with anti-sense expressing vector results in an almost 6-fold reduction in the total protein/total mRNA ratio. Elimination of this effect through the treatment of the AS infected cells with the 2-aminopurine, implies that PKR was directly involved in the inhibition of total translation. Treatment of the U87MGΔEGFR cells infected with AS expressing vector with 2-aminopurine rescued the cells, further supporting the involvement of PKR in cell death. Furthermore cotransfection of a plasmid encoding a transdominant negative mutant of PKR, PKRΔ6 (Koromilas et al. Science 257: 1685-9) with pΔEGFR-AS almost completely abrogated the effect of pΔEGFR-AS transfection alone (FIGS. 12a-b). Transfection of plasmids encoding E3L and K3L, Vaccinia virus proteins that inhibit PKR, had similar effects.

Example 7

Targeted Cell Killing in Lymphoma Cells

Every t(14; 18) translocation has a unique sequence as a result of the different potential breakpoints on the two partner chromosomes and the random insertion of nucleotides at the fusion point ('N' region).

Cell Culture.

Lymphoma cell lines Nalm6: human pre-B-cell line (Hurwitz et al., 1979 Seminars in Oncology 25:447-460); Lam: human B-cell lymphoma which over-expresses bcl-2 due to the translocation t(14;18); and Karpas299: T-cell lymphoma which is characterized by translocation t(2:5) resulting in the expression of the NPM-ALK fusion protein (Fischer et al., 1988 Blood 72:234-240) were used here. All lymphoma cell lines are grown in RPMI 1640 with 10% fetal calf serum (FCS) (Beit Haemek, Israel), 100 µg/L streptomycin, 100,000 U/L penicillin. The HeLa, 3T3 L1 Tet-Off and 293T cell lines are grown in DMEM with 10% FCS, 100 µg/L streptomycin, 100,000 U/L penicillin. The medium for 3T3 L1 Tet-Off is supplemented with 100 µg/ml G418 and 2 µg/ml doxycycline.

Vectors.

A. The 77 nt and 47 nt long antisense and sense oligonucleotides corresponding to the sequences flanking the translocation regions t(14;18) bcl-2/IgH and t(2;5) NPM/ALK, respectively, were synthesized and cloned into XhoI and NsiI sites of the U6 expression vector. (He et al., 1998 J. Natl. Cancer Inst. 90: 1080-1087).

The antisense and sense sequences for the t(2;5) were according to the translocation sequence published in the literature (Morris et al., 1994 Science 263: 1281-1284):
NPM/ALK-Antisense:

```
                                                  SEQ ID No 11
TCGAGGTGCTTCCGGCGGTACACTACTAAGTGCTGTCCACTAATGCA

NPM/ALK-sense:
                                                  SEQ ID No 12
TCGAGTAGTGGACAGCACTTAGTAGTGTACCGCCGGAAGCACATGCA
```

Since there are many potential breakpoints, the sequences of the antisense and sense for t(14;18) translocation were determined by nested PCR (see below):

```
Bcl-2/IgH-antisense:
                                                  SEQ ID No 13
TCGAGGACGTCCATACCGTATCTTCATCCCATTCGCACACAGGGGGTAACGGGGC

GCCGGGTAAGCACCACTGCATTTCAATGCA

Bcl-2/IgH-sense:
                                                  SEQ ID No 14
TCGAGTGAAATGCAGTGGTGCTTACCCGGCGCCCCGTTACCCCCTGTGTGCGAAT

GGGATGAAGATACGGTATGGACGTCATGCA
```

B. For lentiviral vector production the whole U6 cassette was excised by BamHI/EcoRI digestion, filled in with Klenow enzyme and inserted into the XhoI site (filled in) of the lentiviral vector pRRL-PGK-SIN (Deglon et al., 2000 Human Gene Therapy 11:179-190).

Nested PCR.

Genomic DNA was purified from Lam and Nalm-6 cell lines as described (Edwards et al., 1991 Nucleic Acid Research 19: 1349). The first PCR was performed using the following set of primers:

```
                                                  SEQ ID No 15
JH-5'ACCTGAGGAGACGGTGACCAGGGT3'
and
                                                  SEQ ID No 16
PA1-5'AGTTATGGCCTATACACTATTTGT3'.
```

The second PCR utilized the product of the first PCR as a template, and the primers:

```
                                                  SEQ ID No 17
PA2-5'TTGTGAGCAAAGGTGATCGT3'
and
                                                  SEQ ID. No 18
PA3-5'CAGGGTCCCTTGGCCCCAG3'
```

The conditions for the two PCR reactions were the same (100 µM primers, 2.5 mM dNTPs, 1.5 mM MgCl2, 5 min at 94(C; 29 cycles of: 30 sec at 94(C, 30 sec at 55(C and 2 min at 86(C; 7 min at 72(C).

IFNα Treatment.

Cells were seeded onto 6-well plates at a density of $5 \times 10^5$ cells/well and IFNα (500 U/ml) was added. Cells were lysed after 20 h using sample buffer (40% glycerol, 0.2M Tris HCl, pH 6.8, 20% β-Mercaptoethanol, 12% SDS, Bromo-Phenol Blue).

Western Blot Analysis.

Equal amounts of proteins were loaded onto SDS-PAGE. The separated proteins were transferred to a nitrocellulose membrane, probed with the appropriate antibody, and visualized using ECL procedure. Secondary antibodies labeled with HRP were obtained from Jackson Immuno-Research Laboratories, Inc.

PKR Radioactive Kinase Assay.

The procedure was based on the literature (Patel and Sen, 1998) with certain changes. Cells were washed in cold-ice PBS and packed by centrifugation at 600 g for 5 min (adherent cells were trypsinized before). Thereafter, they were lysed in lysis buffer (20 mM Tris HCl, pH 7.5, 5mM $MgCl_2$, 50 mM KCl, 400 mM NaCl, 2 mM DTT, 20% glycerol, 1% Triton X-100, 10 µg/ml aprotinin, 2.4 µg.ml AEBSF). The lysates were centrifuged at 10,000 g for 5 min and the supernatants were assayed for PKR activity. 500 kg aliquots of total protein were immunoprecipitated using monoclonal PKR antibody (Ribogene) in high salt buffer (20 mM Tris HCl, pH 7.5, 50 mM KCl, 400 mM NaCl, 1 mM EDTA, 1 mM DTT, 20% glycerol, 1% Triton X-100, 10 µg/ml aprotinin, 2.4 µg.ml AEBSF) at 4° C. for 1 hr on a rotating wheel. 50 µl of 20% protein A-Sepharose beads were then added and incubation was carried out for a further 1 h. Thereafter, the protein A-Sepharose beads were washed four times in high salt buffer and twice in activity buffer (20 mM Tris HCl, pH 7.5, 2 mM $MgCl_2$, 2 mM $MnCl_2$, 50 mM KCl, 20% glycerol, 1% Triton X-100, 10 µg/ml aprotinin, 2.4 µg.ml AEBSF). The PKR assay was performed in activity buffer to which were added the bead-bound PKR, 500 ng purified eIF2α, 0.1 mM ATP and 10 Ci of [γ-$^{32}$P]ATP. The reaction proceeded at 30° C. for 10 min. PolyI-C at various concentrations (0.1, 1 and 10 µg/ml) was used to activate PKR. The reaction was halted by the addition of sample buffer (40% glycerol, 0.2M Tris HCl, pH 6.8, 20% β-Mercaptoethanol, 12% SDS, Bromo-Phenol Blue). The samples were boiled and separated by 10% SDS-PAGE. The separated proteins were transferred to a nitrocellulose membrane, which was exposed to a phosphorimager plate. The radioactive bands were detected in a phosphorimager (FUJIX, BAS 1000). The same membrane was also probed with PKR antibody (71/10, Ribogene, 1:5000).

PKR Non-Radioactive Kinase Assay.

Cell lysates were prepared as described above. The reaction consisted of 50 µg aliquots of total protein in 100 µl of kinase reaction containing 20 mM Tris-Hcl, pH 7.5, 50 mM KCl, 2 mM MgCl$_2$, 2mM MnCl$_2$, 5% glycerol, 10 mM NaF, 100 μM ATP, 10 μg/ml aprotinin, 2.4 μg.ml AEBSF in the presence of various concentration of pIC. The mixture was incubated on ice for 10 min to allow association of dsRNA with PKR. Then, 500 ng purified eIF2α was added to the reaction and incubated at 30° C. for 20 min. The reaction was halted by the addition of sample buffer. The samples were boiled and separated by 12% SDS-PAGE. The separated proteins were transferred to a nitrocellulose membrane. Phosphorylated substrate was detected by a specific antibody to the phosphorylated form of eIF2α (Research Genetics, 1:10,000). The same membrane was also probed with PKR antibody (71/10, Ribogene, 1:5000).

Lentiviral Vector Production.

2×10$^6$ 293T cells are seeded onto 10 cm plates. The pseudotyped HIV vectors are generated by transient cotransfection of a vector construct containing the GFP gene and the antisense or sense (pRRL-PGK-SIN, 20 μg), with the VSV-G-expressing construct (pMD.G, 10 μg) and the packaging construct (pCMVΔR8.91, 10 μg), using FuGene6™ (Boehringer Mannheim). The medium is collected 48 hr after transfection, and various volumes of medium are used to infect the various cell lines.

Cell Infection.

2×10$^6$ cells are seeded onto non-tissue culture 6-well plates (Falcon) coated with RetroNectin (Takara Shuzo Co, Ltd, Japan) according to the manufacturer's instructions. The medium containing the virus is added into the wells, and GFP expressing cells are visualised by fluorescence microscopy, 48 hr after infection. When antisense/sense-expressing vectors are used to infect the cells, they will be seeded on 96-well plates coated with RetroNectin.

Measurement of Global Translation Level.

Equal numbers of cells will be taken for extraction of total protein and total mRNA (PolyA Tract mRNA Isolation System III, Promega). Total protein concentration is determined by Coomassie blue staining, while total RNA concentration is determined by spectrophotometric analysis at 260/280 nm. The ratio of total protein to total mRNA provides a standardized value for the amount of translation.

Cell Growth Assay.

Cell growth will be determined by the microculture methylene blue assay (Ben Bassat et al., 1995).

Apoptosis Assays.

For FACS analysis, Cells will be stained with Annexin-V-FIOUS +PI according to the manufacturer's instruction (Boehringer Mannheim). For DNA fragmentation analysis, cells will be fix with 70% ethanol for 1 h on ice, and then incubated with PI solution (50 μg/ml PI, 0.1% triton X-100, 100 μg/ml RNAse A, in PBS).

Sequencing of the Translocation Junction t (14; 18) in Lam Cells

In order to sequence the translocation junction in Lam cell line, a nested PCR reaction was performed on genomic DNA purified from Lam and Nalm-6 cells. As expected, no product was obtained using Nalm-6 DNA. Sequencing of the PCR product obtained from Lam DNA revealed the translocation junction between bcl-2 and IgH (FIG. 1). The sequence for the translocation junction in Karpas299 cell line was taken from the literature (Morris et al., 1994).

bcl-2/IgH: Translocation Junction in LAM Cells

```
Bcl2 sequence
                                          SEQ ID No 19
401  CTCCTTCCGC GGGGGCTTTC TCATGGCTGT CCTTCAGGGT
     CTTCCTGAAA
```

Sequence of the fusion point, in which random nucleotides are inserted during chromosome recombination.

```
                                          SEQ ID No 20
451  TGCAGTGGTG CTTAC CCGGC GCCCCGTTAC CCCCTGTGTG
     CGAATGGGAT

IgH CDR3 region sequence
                                          SEQ ID No 21
501  GAAAATACNG TATGGACGTC TGGGGCCAAG GGA
```

Lentiviral Infection of the Nalm6 and Karpas299 Cell Lines

The Nalm6, Lam and Karpas299 cell lines were infected with GFP encoding virus. Lentiviral vector production and infection were performed as described above. Two days after infection the cells expressing GFP were visualized and counted under the fluorescence microscope. The number of cells expressing GFP was divided by total cell number to yield the infection efficiency. When 0.5 ml (out of 8 ml) of medium containing virus was utilized for infection, 50% of the Nalm6 cells were found to be infected, whereas the infection efficiency of Karpas 299 was only 35%. These preliminary results show that genetic material can be introduced into these cell lines using lentiviral vectors. Efforts should however, be made to concentrate the virus in order to improve the yield of infection.

PKR Expression in Lam, Nalm-6 and Karpas 299 Cell Lines

Figure 13:
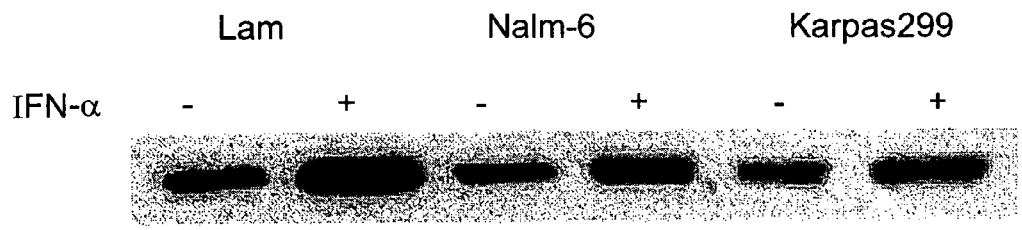
FIG. 13 shows the effect of IFN-α on PKR expression for three, lymphoma cell lines-Lam, Nalm-6 and Karpas 299. A western blot shows enhanced PKR expression in the presence of interferon.

Cells were grown with or without IFN-α (500 U/ml) for 20 h. Thereafter, they were lysed with sample buffer, and 30 μg of total protein was separated by 10% SDS-PAGE. The blot was incubated with anti-PKR (Ribogen). The results are shown in FIG. 13. The results show that IFN-α induces pkr transcription, as expressed by elevated levels of PKR, in Lam, Nalm-6 and Karpas299 cell lines.

PKR Kinase Assay

Figure 14:
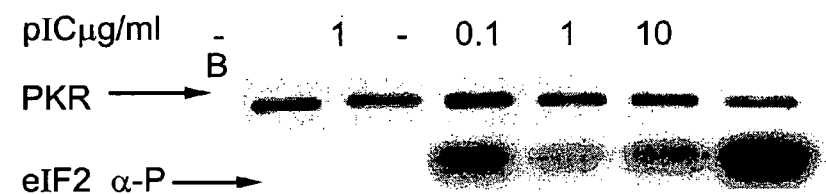
FIG. 14 shows in vitro activation of PKR in karpas 299 lymphoma cells showing the levels of phosphorylated eIF2α/PKR was greatest at 10 μg/ml of Poly I-C.
Figure 14:
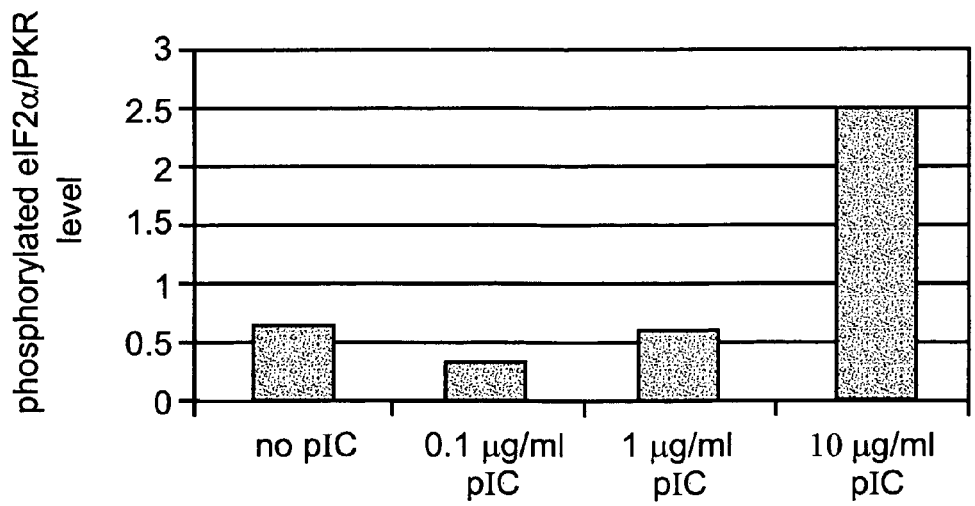

Activation of PKR was examined in Karpas299 cell line treated with IFNα, by a radioactive kinase assay, as described in "Materials and Methods". PKR levels detected in the various samples and eIF2α phosphorylation are shown in FIG. 14A. Normalization of the Substrate phosphorylation to PKR level shows that PKR is activated by 10 μg/ml of pI-C (FIG. 14B).

Figure 15A:
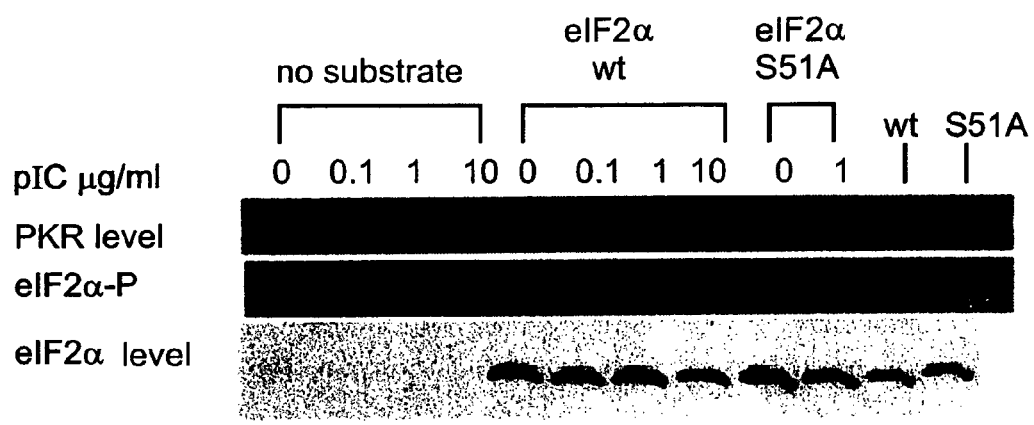
FIG. 15(a) shows activation of PKR in lysates of Karpas299 treated with IFN-α and (b) in the absence of IFN-α.
Figure 15B:
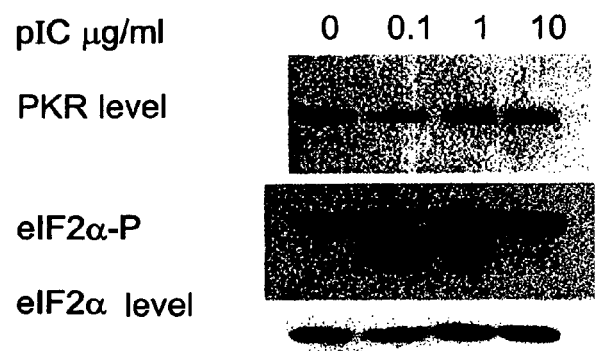

In order to simplify the assay two changes were made: 1) a specific antibody was used for the phosphorylated form of eIF2α instead of using radioactively labeled ATP. 2) The assay was performed on lysates instead of immunoprecipitants. A non-radioactive assay using lysates of Karpas299 treated with IFNα was performed as described above. For controls, the reaction was performed either without any substrate or with a mutant form of eIF2α that can not be phosphorylated (eIF2 αS51A). The results are shown in FIG. 13. The phosphorylated form of eIF2α was detected by a specific antibody only in samples containing both lysate and wt substrate. The highest detection of phosphorylated eIF2α was found in a sample that was subjected to 1 μg/ml of pI-C. No phosphorylated eIF2α was detected in samples that did not contain wt or mutant substrate. Also, no phosphorylated eIF2α was detected in the last two lanes that were loaded solely with the purified substrates, wt or mutant. The results show that specific activation of PKR can be achieved in lysates from Karpas299. Interestingly, when performing the assay on lysates from karpas 299 cells that were not treated with IFNα, activation of PKR was revealed in lower concentrations of pI-C (FIG. 15). The need for higher concentration of pI-C in order to activate PKR may be due to IFNα treatment which causes elevation of PKR expression (FIG. 13).

The above examples are not intended to be limiting but rather are provided to exemplify embodiments of the invention. All references cited herein are incorporated by reference.

What is claimed is:

1. A method for selectively killing glioma cells expressing an mRNA sequence of Δ 2-7 EGFR and also a double stranded RNA dependent protein kinase, the method comprising locally administering to said glioma cells an anti-sense RNA comprising a sequence selected from the group consisting of SEQ ID NO: 7 and 9, wherein said anti-sense RNA forms a double stranded RNA of at least 30 bp with the Δ 2-7 EGFR mRNA in the glioma cells, thereby activating the double stranded RNA dependent protein kinase in the glioma cells and killing the glioma cells.

2. A method according to claim 1, wherein said locally administering comprises administering to said glioma cells a DNA sequence which is transcribed in the glioma cells to provide said anti-sense RNA.

3. A method according to claim 2, wherein the DNA sequence is contained within any of a plasmid, a virus or a liposome or is delivered to the glioma cells as naked DNA or is transcribed from an RNA sequence contained within a retrovirus.

4. A method according to claim 2, wherein the DNA sequence is contained within a virus selected from the group consisting of an adenovirus, vaccinia virus and a herpes virus.

5. A method according to claim 3, wherein the DNA sequence is naked DNA, the naked DNA being attached to a carrier.

6. A method according to claim 1, wherein said antisense RNA is obtained from an RNA sequence encoding said anti-sense RNA wherein said RNA sequence is replicated in the glioma cells to form double stranded RNA.

7. A method according to claim 6, wherein the RNA sequence is contained within a virus.

8. A method according to claim 7, wherein the virus is a lentivirus.

9. A method according to claim 3, wherein the RNA sequence includes a U6 small nuclear RNA promoter.

10. A method according to claim 1, wherein the glioma cells are located in vivo in a subject.

11. A method according to claim 1, wherein the glioma cells are located ex vivo in a culture vessel.

12. A method according to claim 1, further comprising locally administering to the glioma cells, an amount of interferon for activating, and/or elevating levels of, a double stranded RNA dependent protein kinase in the glioma cells.

13. The method of claim 1, wherein said anti-sense RNA forms a double stranded RNA between 30-100 base pairs.

* * * * *

SEQUENCE LISTING

<160> NUMBER OF SEQ ID NOS: 21

<210> SEQ ID NO 1
<211> LENGTH: 36
<212> TYPE: RNA
<213> ORGANISM: Homo sapiens

<400> SEQUENCE: 1
acucaguucu uaucucaccu ucucagaauc cuuuug       36

<210> SEQ ID NO 2
<211> LENGTH: 36
<212> TYPE: DNA
<213> ORGANISM: Homo sapiens

<400> SEQUENCE: 2
caaaagcatt ctgagaaggt gagataagaa ctgagt       36

<210> SEQ ID NO 3
<211> LENGTH: 40
<212> TYPE: RNA
<213> ORGANISM: Homo sapiens

<400> SEQUENCE: 3
acagacauca cuaagucccc uucaaaaaaa auaaaauuca       40

<210> SEQ ID NO 4
<211> LENGTH: 40
<212> TYPE: DNA
<213> ORGANISM: Homo sapiens

<400> SEQUENCE: 4
tgaattttat tttttttgaa ggggtcttag tgatgtctga       40

<210> SEQ ID NO 5
<211> LENGTH: 40
<212> TYPE: RNA
<213> ORGANISM: Homo sapiens

<400> SEQUENCE: 5
cuggugcuuc cggcgguaca cuuccagguc aucaauuguc       40

<210> SEQ ID NO 6
<211> LENGTH: 40
<212> TYPE: DNA
<213> ORGANISM: Homo sapiens

<400> SEQUENCE: 6
gacaattgat gacctggaag tgtaccgccg gaagcaccag       40

<210> SEQ ID NO 7
<211> LENGTH: 40
<212> TYPE: RNA
<213> ORGANISM: Homo sapiens

<400> SEQUENCE: 7
aucugucacc acauaauuac cuuucuuuuc cuccagagcc       40

<210> SEQ ID NO 8
<211> LENGTH: 40
<212> TYPE: DNA
<213> ORGANISM: Homo sapiens

-continued

```
<400> SEQUENCE: 8
ggctctggag gaaaagaaag gtaattatgt ggtgacagat                              40

<210> SEQ ID NO 9
<211> LENGTH: 39
<212> TYPE: DNA
<213> ORGANISM: Artificial sequence
<220> FEATURE:
<223> OTHER INFORMATION: Single strand DNA oligonucleotide used as an
      insert for the cloning of the AS-EGFR construct

<400> SEQUENCE: 9
tctgtcacca cataattacc tttcgtttcc tccagagcc                               39

<210> SEQ ID NO 10
<211> LENGTH: 39
<212> TYPE: DNA
<213> ORGANISM: Artificial sequence
<220> FEATURE:
<223> OTHER INFORMATION: Single strand DNA oligonucleotide used as an
      insert for the cloning of the AS-EGFR construct

<400> SEQUENCE: 10
gctctggagg aaaagaaagg taattatgtg gtgacagat                               39

<210> SEQ ID NO 11
<211> LENGTH: 47
<212> TYPE: DNA
<213> ORGANISM: Artificial sequence
<220> FEATURE:
<223> OTHER INFORMATION: Single strand DNA oligonucleotide

<400> SEQUENCE: 11
tcgaggtgct tccggcggta cactactaag tgctgtccac taatgca                      47

<210> SEQ ID NO 12
<211> LENGTH: 47
<212> TYPE: DNA
<213> ORGANISM: Artificial sequence
<220> FEATURE:
<223> OTHER INFORMATION: Single strand DNA oligonucleotide

<400> SEQUENCE: 12
tcgagtagtg gacagcactt agtagtgtac cgccggaagc acatgca                      47

<210> SEQ ID NO 13
<211> LENGTH: 85
<212> TYPE: DNA
<213> ORGANISM: Artificial sequence
<220> FEATURE:
<223> OTHER INFORMATION: Single strand DNA oligonucleotide

<400> SEQUENCE: 13
tcgaggacgt ccataccgta tcttcatccc attcgcacac aggggqtaac ggggcgccgg        60 gtaagcacca ctgcatttca atgca                                              85

<210> SEQ ID NO 14
<211> LENGTH: 85
<212> TYPE: DNA
<213> ORGANISM: Artificial sequence
<220> FEATURE:
<223> OTHER INFORMATION: Single strand DNA oligonucleotide

<400> SEQUENCE: 14
tcgagtgaaa tgcagtggtg cttacccggc gccccgttac ccctgtgtg cgaatgggat         60
```

```
gaagatacgg tatggacgtc atgca                                                 85
```

```
<210> SEQ ID NO 15
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 15
acctgaggag acggtgacca gggt                                                  24

<210> SEQ ID NO 16
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 16
agttatggcc tatacactat ttgt                                                  24

<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17
ttgtgagcaa aggtgatcgt                                                       20

<210> SEQ ID NO 18
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 18
cagggtccct tggccccag                                                        19

<210> SEQ ID NO 19
<211> LENGTH: 50
<212> TYPE: DNA
<213> ORGANISM: Homo sapiens
<220> FEATURE:
<221> NAME/KEY: misc_feature
<223> OTHER INFORMATION: sequence of the Bcl-2 translocation junction
      from LAM cells

<400> SEQUENCE: 19
ctccttccgc gggggctttc tcatggctgt ccttcagggt cttcctgaaa                      50

<210> SEQ ID NO 20
<211> LENGTH: 50
<212> TYPE: DNA
<213> ORGANISM: Homo sapiens
<220> FEATURE:
<221> NAME/KEY: misc_feature
<223> OTHER INFORMATION: Sequence of random nucleotides inserted into
      the translocation junction by chromosome recombination

<400> SEQUENCE: 20
tgcagtggtg cttacccggc gccccgttac ccctgtgtg cgaatgggat                       50

<210> SEQ ID NO 21
```

```
<211> LENGTH: 33
<212> TYPE: DNA
<213> ORGANISM: Homo sapiens
<220> FEATURE:
<221> NAME/KEY: misc_feature
<223> OTHER INFORMATION: sequence from the IgH CDR3 part of the
      translocation in LAM cells
<220> FEATURE:
<221> NAME/KEY: misc_feature
<222> LOCATION: (9)..(9)
<223> OTHER INFORMATION: Any nucleotide

<400> SEQUENCE: 21
gaaaatacng tatggacgtc tggggccaag gga                                   33
```